(12) United States Patent
Watt et al.

(10) Patent No.: US 9,873,670 B2
(45) Date of Patent: Jan. 23, 2018

(54) ARYLQUINOLINE AND ANALOG COMPOUNDS AND USE THEREOF TO TREAT CANCER

(71) Applicant: UNIVERSITY OF KENTUCKY RESEARCH FOUNDATION, Lexington, KY (US)

(72) Inventors: David S. Watt, Lexington, KY (US); Chunming Liu, Lexington, KY (US); Vivek Rangnekar, Nicholasville, KY (US); Vitaliy M. Sviripa, Lexington, KY (US); Ravshan Burikhanov, Lexington, KY (US); Wen Zhang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/036,916

(22) PCT Filed: Nov. 21, 2014

(86) PCT No.: PCT/US2014/066796
§ 371 (c)(1),
(2) Date: May 16, 2016

(87) PCT Pub. No.: WO2015/077550
PCT Pub. Date: May 28, 2015

(65) Prior Publication Data
US 2016/0280652 A1    Sep. 29, 2016

Related U.S. Application Data

(60) Provisional application No. 61/907,817, filed on Nov. 22, 2013.

(51) Int. Cl.
| | | |
|---|---|---|
| *C07D 215/38* | (2006.01) | |
| *C07D 215/06* | (2006.01) | |
| *A61K 31/47* | (2006.01) | |
| *C07D 495/04* | (2006.01) | |
| *C07D 215/227* | (2006.01) | |
| *C07D 215/36* | (2006.01) | |

(52) U.S. Cl.
CPC ............ *C07D 215/38* (2013.01); *A61K 31/47* (2013.01); *C07D 215/06* (2013.01); *C07D 215/227* (2013.01); *C07D 215/36* (2013.01); *C07D 495/04* (2013.01)

(58) Field of Classification Search
CPC ........................... C07D 215/38; C07D 215/06
See application file for complete search history.

(56) References Cited

U.S. PATENT DOCUMENTS

2007/0077644 A1    4/2007    Yoshio

FOREIGN PATENT DOCUMENTS

WO    2009/127417 A1    10/2009

OTHER PUBLICATIONS

Walser et al., J. Heterocyclic Chemistry (1975), 12(2), 351-8.
Mphahlele et al., Molecules (2011), 16, 8958-8972.
L. Fu et al., "Novel and efficient synthesis of substituted quinoline-1-oxides and the complex compounds $SnL_2Cl_2$ (L=2-aminoquinoline-1-oxides) with the aid of stannous chloride," Tetrahedron 68 (2012), 7782-7786.
Burikhanov et al., "Arylquins target vimentin to triggar Par-4 secretion for tumor cell apoptosis," Nature Chemical Biology, Sep. 14, 2014, vol. 10, No. 11, pp. 924-926.
International Search Report and Written Opinion issued in Application No. PCT/US2014/066796 dated Feb. 15, 2015.

*Primary Examiner* — Samira Jean-Louis
(74) *Attorney, Agent, or Firm* — McDermott Will & Emery LLP

(57) ABSTRACT

The subject technology relates to arylquinoline compounds and their use for treating cancer or cancer metastasis. The compounds of the subject technology promote cells to secrete a pro-apoptotic tumor suppressor, i.e., prostate apoptosis response-4 (Par-4), which in turn promote apoptosis in cancer cells or metastatic cells.

13 Claims, 5 Drawing Sheets

Legend of reagents: a, arylacetonitrile, tert-BuOK, DMF, 90°C, 3-4h; b, 2(2'-fluorophenyl)acetyl chloride, Et$_3$N, reflux 2h and then K$_2$CO$_3$, DMF, 90°C, 4h; c, 2,4-bis(4-methoxyphenyl)-2,4-dithioxo-1,3,2,4-dithiadiphosphetane (Lawesson's reagent), dioxane, reflux 5h; d, (+)-biotinyl-iodoacetamidyl-3,6-dioxaoctanediamine, K$_2$CO$_3$, DMF, 12h; e, POCl$_3$, reflux, 3h; f, Zn, CH$_3$CO$_2$H, 75°C, 1 h.

ARYLQUINOLINE AND ANALOG COMPOUNDS AND USE THEREOF TO TREAT CANCER

CROSS-REFERENCE TO RELATED APPLICATION

This application is a U.S. National Phase under 35 U.S.C. §371 of International Application No. PCT/US2014/066796, filed Nov. 21, 2014, which claims the benefit of U.S. Provisional Application No. 61/907,817, filed Nov. 22, 2013, the entire disclosures of which are hereby incorporated by reference herein.

STATEMENT REGARDING FEDERALLY SPONSORED RESEARCH

This work was supported by National Center for Research Resources in a grant entitled "COBRE Center for Biomedical Research Excellence" grant P20 RR020171; and NIH/NCI R01 CA60872 (to VMR). The government has certain rights in the subject technology.

TECHNICAL FIELD

The present invention relates to compounds that treat cancer and/or treat or prevent cancer metastasis. In particular, the subject technology is directed to arylquinoline compounds and analogs thereof such as arylquinolone or arylthioquinolone compounds, described as "arylquin" compounds, that promote cells to secrete a pro-apoptotic tumor suppressor, such as prostate apoptosis response-4 (Par-4), which promotes apoptosis in cancer cells or metastatic cells.

BACKGROUND

Lung cancer is the most frequently diagnosed cancer and the leading cause of cancer-related deaths in the world. The most common alterations in lung cancer include activating mutations in ras genes and inactivating mutations in the p53 gene. Lung tumor cells with p53 mutations or deletions often develop resistance to chemotherapy and radiation therapy, leading ultimately to the death of the patients. Notably, such p53-deficient cancer cells are susceptible to apoptosis by the proapoptotic tumor suppressor, Par-4.

Par-4 is a tumor suppressor protein that induces apoptosis in diverse cancer cells but not in normal cells. Par-4 is ubiquitously expressed in normal cells and tissues, but is sequestered by an intermediary filament protein, vimentin, and hence, circulating levels of Par-4 are generally low. If it were secreted by normal cells at appreciably higher levels than normal, certain cancer cells would be susceptible to its effects. Extracellular Par-4 binds a receptor GRP78, which appears only on the cancer cell surface, and induces apoptosis by caspase-dependent mechanisms. In contrast, normal cells express low to undetectable levels of basal or inducible cell-surface GRP78 and are resistant to apoptosis by extracellular Par-4.

Therefore, there is a need for compounds that are Par-4 secretagogues and promote the secretion of Par-4 which in turn promotes apoptosis in cancer cells and metastatic cells.

SUMMARY OF THE DISCLOSURE

Advantages of the subject technology include arylquinoline and analog compounds and compositions for the treatment of cancer or for the treatment or inhibition of cancer metastasis in a subject in need thereof comprising administering to the subject an effective amount of the compound or a pharmaceutically acceptable salt thereof or a composition thereof.

Other advantages of the subject technology include compounds for use in promoting the secretion of Prostate Apoptosis Response-4 (PAR-4) from cells or for use in promoting apoptosis of a cancer cell in a subject comprising administering to the subject an effective amount of an arylquinoline or analog compound or a pharmaceutically acceptable salt thereof or a composition thereof.

In one aspect of the subject technology, the arylquinoline is a compound according to Formula (I):

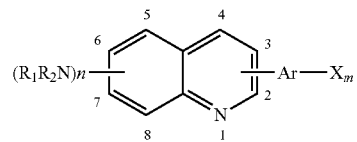

(I)

or a pharmaceutically acceptable salt thereof; wherein n is 1, 2, 3, 4, 5, or 6, for each $NR_1R_2$, $R_1$ and $R_2$ are independently H, alkyl, alkoxy, aryl, heteroaryl; Ar is aryl or heteroaryl, which can be further substituted with halogen, amino, alkylamino, dialkylamino, arylalkylamino, N-oxides of dialkylamino, trialkylammonium, mercapto, alkylthio, alkanoyl, nitro, nitrosyl, cyano, alkoxy, alkenyloxy, aryl, heteroaryl, sulfonyl, sulfonamide, $CONR_3R_4$, $NR_3CO(R_4)$, $NR_3COO(R_4)$, $NR_3CONR_4R_5$ where $R_3$, $R_4$, $R_5$, are independently, H, alkyl, aryl, heteroaryl or a fluorine; X represents halogen; m is 1, 2, 3, 4, or 5.

In one aspect of the present disclosure, n is 1 to 3; m is 1 to 3 and X is selected from fluorine or chlorine, e.g. X is one, two or three fluorine substituents, or X is one, two or three chlorine substituents, or X represents at least one fluorine and at least one chlorine on Ar. In various embodiments, the compound of Formula (I) includes wherein n is at least 2 or 2 and one $NR_1R_2$ group is at the 2 position of the quinoline ring and another $NR_1R_2$ group is at the 7 position of the quinoline ring; and Ar-Xm is at the 3 position of the quinoline ring. In other embodiments, Ar is phenyl, m is 2 and X is selected from fluoro or chloro. In further embodiments, m is 1 and the Ar-Xm group at the 3 position of the quinoline ring is an ortho fluoro or ortho chloro phenyl group. In still other embodiments, the Ar-Xm group at the 3 position is a halogen substituted heteroaryl, e.g., pyridyl, pyrolidyl, piperidyl, or pyrimidyl having one or more halogen substituents. For each of the embodiments, each of $R_1$ and $R_2$ of each $NR_1R_2$ can be independently H, or a lower alkyl.

In another aspect, the subject technology relates to compounds where the Ar-Xm group is located at the 3 position of the quinoline, quinolone or thioquinolone ring and Ar is a phenyl group such as shown in formulas (II) or (III):

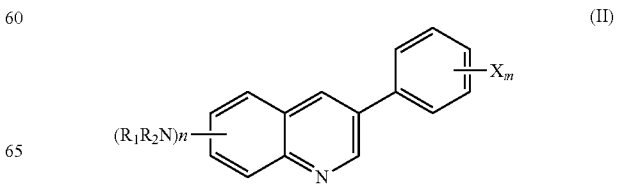

(II)

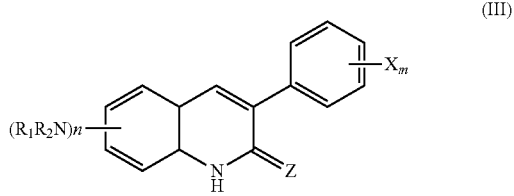

or a pharmaceutically acceptable salt thereof. In Formulas (II) and (III), Z is O or S; and n, $R_1$, $R_2$, X and m are as defined for the compound of Formula (I). The compounds of Formula (III) are arylquinolones and arylthioquinolones when Z is O or S, respectively, and are useful in the same manner as the compounds according to Formula (I). For ease of reference, the compounds of Formulas (I), (II), (III) will be referred to herein as arylquinoline or arylquin compounds.

In various embodiments, the compounds of Formula (II) and Formula (III) have n as 1, 2, or 3 and m as 1, 2, or 3, e.g., the compounds include one $NR_1R_2$ group at the 2 position of the quinoline ring and another $NR_1R_2$ group at the 7 position of the quinoline ring, and X is selected from fluoro or chloro. In other embodiments, the compounds of Formula (II) or (III) have n as 2, m as 2 and X selected from fluoro or chloro. In still further embodiments, the compounds of Formula (II) or (III) have n as 2, m as 1 and X selected as chloro or fluoro at the ortho position of the phenyl ring. For each of the embodiments, each $R_1$ and $R_2$ of each $NR_1R_2$ can be independently H, or a lower alkyl.

Another aspect of the subject technology includes a biotinylated derivative or other detectably labeled alternative of each of Formulas (I), (II) and (III) and their various embodiments.

In another aspect, the subject technology relates to pharmaceutical compositions of arylquinoline compounds, e.g., one or more compounds of Formula (I), Formula (II) and/or Formula (III), and/or one or more pharmaceutically acceptable salts thereof, in combination with a pharmaceutical additive, e.g., a pharmaceutically acceptable carrier and/or excipient. In an embodiment related to this aspect, the subject technology relates to a pharmaceutical composition including an effective amount of at least one arylquinoline compound.

In another aspect, the subject technology relates to a method of treating cancer and/or treating or inhibiting cancer metastasis in a subject, e.g., a human. In an embodiment relating to this aspect, a therapeutically effective amount of one or more arylquinoline compounds, pharmaceutical salts and/or compositions thereof is administered to a subject in need thereof to treat cancer and/or treat or inhibit cancer metastasis in the subject.

In another aspect, the subject technology relates to a method for promoting secretion of Prostate Apoptosis Response-4 (Par-4) from cells or promoting apoptosis of cancer cells in a subject in need thereof by administering to the subject an effective amount of one or more arylquinoline compounds or compositions in accordance with the subject technology.

In another aspect, the subject technology relates to a method for screening for compounds that inhibit vimentin binding to PAR-4, comprising exposing a solution including vimentin and PAR-4 to a test compound and detecting the level of vimentin-PAR-4 complex formation by Western blot analysis, for example.

In another aspect, the subject technology relates to a kit which includes the compounds of the subject technology. In an embodiment related to this aspect, the kit includes one or more compounds of Formula (I), (II) and/or (II). In another embodiment, the kit includes one or more other therapeutic compounds for use in combination therapies.

Additional advantages of the subject technology will become readily apparent to those skilled in this art from the following detailed description, wherein only the preferred embodiment of the disclosure is shown and described, simply by way of illustration of the best mode contemplated of carrying out the disclosure. As will be realized, the disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 4A is a bar graph showing cell surface GRP78 levels in cancer cells treated with CM from MEFs exposed to Arylquin 1. Par-4+/+ MEFs or Par-4-/- MEFs were treated with vehicle or Arylquin 1 (500 nM) for 24 h. The CM from these MEFs was incubated with the indicated cancer cells for 24 h. The cancer cells were then subjected to FACS analysis for cell surface GRP78 expression. Data shown represent mean values of three experiments±s.d. Asterisks (**) or (*) indicate statistical significance (P<0.0001) or (P<0.001), respectively, based on two-way ANOVA with data normality and equality of variance assumptions. FIG. 4B is a bar graph showing the apoptotic activity of secreted Par-4 is inhibited by the presence of a neutralizing antibody against cell surface GRP78. Par-4+/+ MEFs or Par-4−/− MEFs were treated with vehicle or Arylquin 1 (Aq, 500 nM) for 24 h. The CM from these cells was then treated with GRP78 antibody (GRP78 Ab) or control IgG antibody (Control Ab) and incubated with the indicated cancer cells. After 24 h, the cancer cells were scored for apoptosis by ICC for active caspase-3. Apoptosis data shown represent mean values of three experiments±s.d. Asterisks (**) or (*) indicate statistical significance (P<0.0001) or (P<0.001), respectively, based on two-way ANOVA.

DETAILED DESCRIPTION OF THE DISCLOSURE

Figure 1:
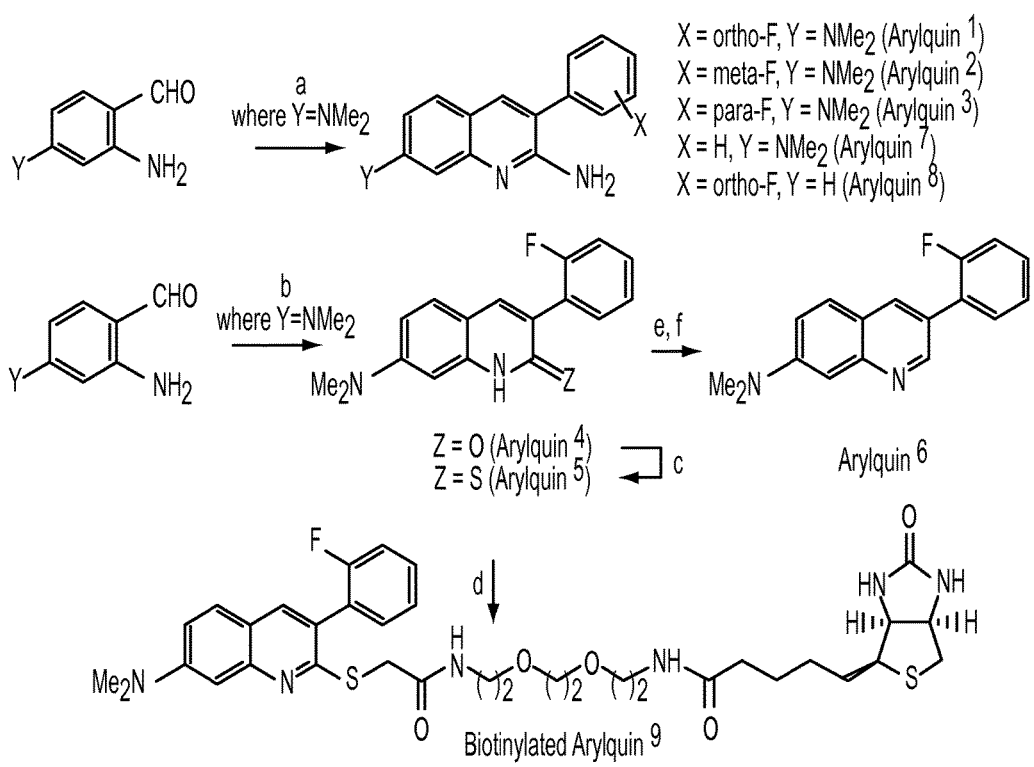
FIG. 1 is an exemplary illustration showing methods for synthesis of arylquinolines, arylquinolones, and arylthioquinolones.

In general, the subject technology relates to Par-4 secretagogues that induce the release of Par-4 from normal cells thereby triggering the paracrine apoptosis of cancer cells. In accordance with the subject technology, certain arylquinoline compounds have been identified as Par-4 secretagogues which induce or promote Par-4 secretion at low (nanomolar) concentrations from both normal lung fibroblasts and epithelial cells. The arylquinoline compounds and their pharmaceutically acceptable salts and compositions are useful for the treatment of colorectal cancer, prostate cancer, brain cancer, liver cancer, breast cancer and lung cancer. In particular, the arylquinoline compounds and their pharmaceutically acceptable salts and compositions are particularly useful in the treatment of lung cancer and prostate cancer.

The Par-4 gene was first identified in 1994 in prostate cancer cells undergoing apoptosis. This gene encodes a pro-apoptotic protein, Prostate Apoptosis Response-4 or Par-4, which is remarkably effective in inducing cancer cell apoptosis and tumor regression in animal models. Par-4 does not affect normal cells. Par-4 protein is secreted in cell culture-conditioned medium (CM) or systemically in mice by normal cells, and extracellular Par-4 binds to its receptor GRP78 on the cancer cell surface and induces apoptosis. Normal cells express low to undetectable levels of cell surface GRP78 and are resistant to apoptosis by extracellular Par-4.

Par-4 induces apoptosis in many types of cancer cells. For cancer cells that may be resistant to direct apoptosis by Par-4, overexpression of Par-4 in these cells renders them supersensitive to a broad range of apoptotic insults, including chemotherapeutic agents, TNF, or ionizing radiation. Applicants have also found that GRP78 levels can be increased on the surface of diverse cancer cells to overcome Par-4-resistance by inhibition of NF-κB activity, which is usually elevated in most cancer cells. Therefore, the arylquinoline compounds of the subject technology can be administered either alone or in combination with a second active ingredient such as a chemotherapeutic agent or an NF-κB inhibitor for treating cancer or cancer metastasis.

As the baseline levels of Par-4 secreted by normal cells are generally inadequate to cause massive apoptosis in cancer cell cultures, secretogogues that bolster the release of Par-4 would constitute an important therapeutic advance. The subject technology thus relates to a new class of "small-molecule" secretagogues, that promote the desired secretion of Par-4 in vitro and in vivo by selectively targeting an intermediate filament protein, vimentin.

The arylquinoline compounds of the present disclosure include compounds according to Formula (I):

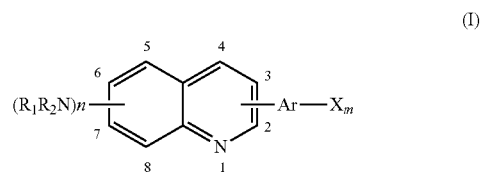

(I)

wherein n is 1, 2, 3, 4, 5, or 6, for each $NR_1R_2$, $R_1$ and $R_2$ are independently H, alkyl, alkoxy, aryl, heteroaryl; Ar is aryl, e.g., phenyl, naphthyl, and heteroaryl, e.g., pyridyl, pyrolidyl, piperidyl, pyrimidyl, indolyl, thienyl, which can be further substituted with halogen, amino, alkylamino, dialkylamino, arylalkylamino, N-oxides of dialkylamino, trialkylammonium, mercapto, alkylthio, alkanoyl, nitro, nitrosyl, cyano, alkoxy, alkenyloxy, aryl, heteroaryl, sulfonyl, sulfonamide, $CONR_3R_4$, $NR_3CO(R_4)$, $NR_3COO(R_4)$, $NR_3CONR_4R_5$ where $R_3$, $R_4$, $R_5$, are independently, H, alkyl, aryl, heteroaryl or a fluorine; X represents halogen, e.g., a fluorine, chlorine, bromine, or iodine substituent; m is 1, 2, 3, 4, 5. This embodiment also includes pharmaceutically acceptable salts of Formula (I).

In one aspect of the present disclosure, n is 1 to 3; m is 1 to 3 and X is selected from fluorine or chlorine, e.g. X is one, two or three fluorine substituents, or X is one, two or three chlorine substituents, or X represents at least one fluorine and at least one chlorine on Ar. In various embodiments, the compound of Formula (I) includes wherein n is at least 2 or 2 and one $NR_1R_2$ group is at the 2 position of the quinoline ring and another $NR_1R_2$ group is at the 7 position of the quinoline ring; and Ar-Xm is at the 3 position of the quinoline ring. In other embodiments, Ar is phenyl, m is 2 and X is selected from fluoro or chloro. In further embodiments, m is 1 and the Ar-Xm group at the 3 position of the quinoline ring is an ortho fluoro or ortho chloro phenyl group. In still other embodiments, the Ar-Xm group at the 3 position is a halogen substituted heteroaryl, e.g., pyridyl, pyrolidyl, piperidyl, or pyrimidyl having one or more halogen substituents. For each of the embodiments, each of $R_1$ and $R_2$ of each $NR_1R_2$ can be independently H, or a lower alkyl.

In another aspect, the subject technology relates to compounds where the Ar-Xm group is located at the 3 position of the quinoline ring and Ar is a phenyl group such as shown in formulas (II) or (III):

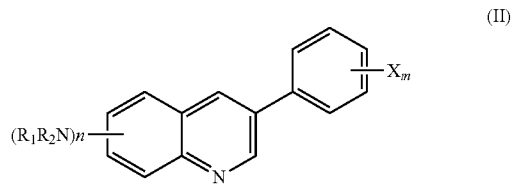

(II)

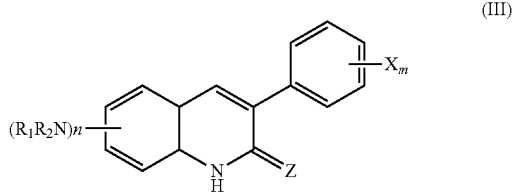
(III)

or a pharmaceutically acceptable salt thereof; wherein Z is O or S; and n, $R_1$, $R_2$, X and m are as defined for the compound of Formula (I).

In one aspect of this embodiment, the compounds of Formula (II) and Formula (III) have n as 1, 2, or 3 and m as 1, 2, or 3, e.g., the compounds include one $NR_1R_2$ group at the 2 position of the quinoline ring and another $NR_1R_2$ group at the 7 position of the quinoline ring, and X is selected from fluoro or chloro. In other embodiments, the compounds of Formula (II) or (III) have n as 2, m as 2 and X selected from fluoro or chloro. In still further embodiments, the compounds of Formula (II) or (III) have n as 2, m as 1 and X selected as chloro or fluoro at the ortho position of the phenyl ring. For each of the embodiments, each $R_1$ and $R_2$ of each $NR_1R_2$ can be independently H, or a lower alkyl.

Another aspect of the subject technology includes a biotinylated derivative or other detectably labeled alternative of each of Formulas (I), (II) and (III) and their various embodiments.

Particular arylquinoline compounds of the subject technology include 3-(2-fluorophenyl)-$N^7,N^7$-dimethylquinoline-2,7-diamine (Arylquin 1); 3-(3-fluorophenyl)-$N^7,N^7$-dimethylquinoline-2,7-diamine (Arylquin 2); 3-(4-fluorophenyl)-$N^7,N^7$-dimethylquinoline-2,7-diamine (Arylquin 3); 7-(dimethylamino)-3-(2-fluorophenyl)quinolin-2(1H)-one (Arylquin 4); 7-(dimethylamino)-3-(2-fluorophenyl)quinoline-2(1H)-thione (Arylquin 5); 3-(2-fluorophenyl)-N,N-dimethylquinolin-7-amine (Arylquin 6); 3-(2-fluorophenyl)quinolin-2-amine (Arylquin 8); N-(2-(2-(2-(2-(7-(dimethylamino)-3-(2-fluorophenyl)quinolin-2-ylthio) acetamido)ethoxy)ethoxy)ethyl)-5-(2-oxohexahydro-1H-thieno[3,4-d]imidazol-4-yl)pentanamide (Biotinylated Arylquin 9).

One of these novel secretagogues, namely Arylquin-1 (FIG. 1), causes particularly robust secretion of Par-4 protein from normal cells and elevates systemic levels of Par-4, thereby providing an effective strategy for the induction of apoptosis of circulating cancer cells as well as the inhibition of the growth of primary and metastatic tumors.

For example, lung cancer, the leading cause of cancer deaths in the US, is commonly associated with oncogenic K-Ras and loss of tumor suppressor p53 function contributing to therapy resistance. Lung cancer cells that express oncogenic Ras or are deficient in p53 function are, however, sensitive to apoptosis by the tumor suppressor protein Par-4. Applicants have found that elevated levels of Par-4 secreted from the normal cells in response to Arylquin-1 are adequate to induce paracrine apoptosis of p53-wild type and p53-deficient lung cancer cells as well as those expressing oncogenic K-ras. These findings imply that secretagogues like Arylquin-1 functionally trigger the secretion of Par-4 from normal cells to induce apoptosis of lung cancer cells. Applicants have further found that endogenous vimentin binds to and sequesters Par-4, and that the Arylquin-1 secretagogue functions by binding to vimentin and releasing Par-4 for secretion.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

To facilitate an understanding of the present subject technology, a number of terms and phrases are defined below:

The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

The term "treat" and "treatment" refer to both therapeutic treatment and prophylactic, inhibition or preventative measures, wherein the object is to inhibit, prevent or slow down (lessen) an undesired pathological change or disorder, such as the development or spread of cancer. For purpose of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, "treatment" can include a qualitative or quantitative reduction (e.g., by at least 10%, 20%, 30%, 40%, 50%, 60%, 70%, 80%, 90%, 95%, or more) in the tumor or metastases size or reduce, inhibit, or prevent metastatic growth. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the subject technology that (i) treats, inhibits, or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may be reduce the number of cancer cells; reduce the tumor size; inhibit (i.e., slow to some extent and preferably stop) cancer cell infiltration into peripheral organs; inhibit (i.e., slow to some extent and preferably prevent or stop) tumor metastasis; inhibit, to some extent, tumor growth; and/or relieve to some extent one or more of the symptoms associated with the cancer. To the extent the drug may prevent growth, inhibit, and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatome, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "prodrug" as used in this application refers to a precursor or derivative form of a compound of the disclosure that may be less cytotoxic to cells compared to the parent compound or drug and is capable of being enzymatically or hydrolytically activated or converted into the more active parent form. The prodrugs of this disclosure include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" as used herein also includes halo-substituted alkyls.

Unless the number of carbons is otherwise specified, "lower alkyl" refers to an alkyl group, as defined above, but having from one to about ten carbons ($C_1$-$C_{10}$), e.g., from one to about six carbon atoms ($C_1$-$C_6$) in its backbone structure. Likewise, "lower alkenyl" "loweralkyl, "lower amino", "lower alkynyl", etc. have similar chain lengths.

Therapeutic Agents

Disclosed herein are arylquinoline compounds, i.e., compounds of Formula (I), (II) and (III), and their use in treating cancer cells or in treating, or inhibiting metastatic cells. Such compounds of the subject technology are Par-4 secretagogues, i.e., promote secretin of Par-4 from cells, which promote apoptosis in cancer cells or metastatic cells. Such compounds are described as "arylquins" as a general descriptor of Par-4 secretagogues. Thus, in an embodiment, the compounds of the subject technology are useful in treating cancers including, but not limited to, colorectal cancer, liver cancer, breast cancer and lung cancer.

Synthesis

The compounds of the subject technology, including compounds of Formula (I) to Formula (II), may be prepared by methods disclosed herein or any other method known in the art. One of ordinary skill in the art will know how to modify procedures to obtain the analogs of the subject technology. In addition, compounds may be prepared using the methods described below and in Example 1 or modified versions thereof.

FIG. 1 is a schematic of the general synthesis of certain arylquinoline compounds of the subject technology. Additional arylquinoline compounds of the subject technology can be made by similar methods or known synthetic procedures known in the art in light of the subject technology.

The subject technology also encompasses biotinylated derivatives of the arylquinoline compounds. Such biotinylated derivatives are useful in identifying the molecular target for these agents. Compounds encompassed by Formulas (I), (II) and (II) can be synthesized and converted to biotinylated derivatives.

In certain embodiments of the subject technology, the arylquinoline compounds of the disclosure, or a pharmaceutically acceptable salt, solvate, hydrate or prodrug thereof, inhibit the growth or spread of cancer cells by promoting apoptosis in them.

Metabolites of Compounds of the Disclosure

Also falling within the scope of this disclosure are the in vivo metabolic products of Formulas (I) to (II) described herein. Such products may result for example from the oxidation, reduction, hydrolysis, amidation, deamidation, esterification, deesterification, enzymatic cleavage, and the like, of the administered compound.

Accordingly, the disclosure includes metabolites of compounds of Formulas (I) to (II), including compounds produced by a process comprising contacting a compound of this disclosure with a mammal for a period of time sufficient to yield a metabolic product thereof.

Metabolite products typically are identified by preparing a detectably labeled, for example a radiolabeled (e.g., C or H isotope) compound of the disclosure, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are detectably labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies, which are well known to those skilled in the art. The metabolite products, so long as they are not otherwise found in vivo, are useful in diagnostic assays for therapeutic dosing of the compounds of the disclosure.

Prodrugs of the Compounds of the Disclosure

In addition to compounds of the subject technology, the disclosure also includes pharmaceutically acceptable prodrugs of such compounds. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the subject technology. The amino acid residues include but are not limited to the 20 naturally occurring amino acids commonly designated by three letter symbols and also includes phosphoserine, phosphothreonine, phosphotyrosine, 4-hydroxyproline, hydroxyzine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Pharmaceutical Compositions

The subject technology also encompasses pharmaceutical compositions comprising at least one arylquinoline compounds, e.g., one or more compounds of Formula (I), (II), and/or Formula (III) and/or one or more pharmaceutically acceptable salts thereof, in combination with a pharmaceutical carrier or excipient. In one embodiment of the subject technology, the pharmaceutical compositions comprise an effective amount of at least one such compound. In another embodiment, the pharmaceutical composition comprises one or more compounds of Formula (III), e.g., Arylquin-1, and a pharmaceutically acceptable carrier.

While it may be possible for compounds of the subject technology to be administered as the raw chemical, it is preferable to present them as a pharmaceutical composition. According to a further aspect, the subject technology provides a pharmaceutical composition comprising a compound or mixture of compounds of Formula (I) to Formula (II) or a pharmaceutically acceptable salt, solvate, hydrate, prodrug or metabolite thereof, together with one or more pharmaceutical carrier, excipient or additive and optionally one or more other therapeutic ingredients. The carrier(s) must be "acceptable" in the sense of being compatible with the other ingredients of the formulation and not deleterious to the recipient thereof. The term "pharmaceutically acceptable carrier" includes vehicles and diluents.

To prepare the pharmaceutical compositions, a therapeutically effective amount of one or more of the arylquinoline compounds according to the subject technology may be intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

In one embodiment, the compositions are prepared with carriers that will protect the active compound(s) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The pharmaceutically acceptable carrier may take a wide variety of forms, depending on the route desired for administration, for example, oral or parenteral (including intravenous). Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension. Other methods of preparation well known by those of ordinary skill may also be used in this aspect of the subject technology.

In an embodiment, the composition of the subject technology enables sustained, continuous delivery of a compound of Formula (I) to Formula (II) or a pharmaceutically acceptable salt, solvate, hydrate, prodrug or metabolite thereof, to tissues adjacent to or distant from an administration site. The biologically-active agent is capable of providing a local or systemic biological, physiological or therapeutic effect. For example, a compound of Formula (I) to Formula (II) or a pharmaceutically acceptable salt, solvate, hydrate, prodrug or metabolite thereof, may act to kill cancer cells, or cancer stem cells or to control or suppress tumor growth or metastasis, among other functions.

Formulations and Dosages for Administration

Pharmaceutical formulations based upon arylquinoline compounds of the subject technology comprise at least one of the compounds of Formula (I) to Formula (III) or a pharmaceutically acceptable salt, solvate, hydrate, prodrug or metabolite thereof, in a therapeutically effective amount for treating neoplasia, cancer and other diseases and conditions that may benefit from induced Par-4 secretion, optionally in combination with a pharmaceutically acceptable additive, carrier and/or excipient. One of ordinary skill in the art will recognize that a therapeutically effective amount of one of more compounds according to the subject technology will vary with the condition to be treated, its severity, the treatment regimen to be employed, the pharmacokinetics of the agent used, as well as the patient (animal or human) treated.

Exemplary formulations are well known to those skilled in the art, and general methods for preparing them are found in any standard pharmacy school textbook, for example, Remington: THE SCIENCE AND PRACTICE OF PHARMACY, 21st Ed., Lippincott. The formulations of the subject technology may conveniently be presented in unit dosage form and may be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations are well known to those skilled in the art, and general methods for preparing them are found in any standard pharmacy school textbook, for example, Remington: THE SCIENCE AND PRACTICE OF PHARMACY, 21st Ed., the entire disclosure of which is incorporated herein by reference.

The concentration of active compound of the subject technology, i.e., at least one of the compounds of Formula (I) to Formula (III) or a pharmaceutically acceptable salt, solvate, hydrate, prodrug or metabolite thereof, in the drug composition will depend on absorption, distribution, inactivation, and excretion rates of the drug as well as other factors known to those of skill in the art. It is to be noted that dosage values will also vary with the severity of the condition to be alleviated. The composition may be administered at once, or may be divided into a number of smaller doses to be administered at varying intervals of time.

Oral compositions will generally include an inert diluent or an edible carrier. They may be enclosed in gelatin-capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following non-limiting ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or fruit flavoring. When the dosage unit form is a capsule, it can contain, in addition to any of the above, a liquid carrier such as fatty oil. In addition, dosage unit forms can contain various other materials which modify the physical form of the dosage unit, for example, coatings of sugar, shellac, or enteric agents.

The tablets, for example, may optionally be coated or scored and may be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in Remington: The Science and Practice of Pharmacy, 21st Ed.

The active compound may also be administered as a component of an elixir, suspension, syrup, wafer or the like. Syrup may contain, in addition to the active compounds, sucrose or fructose as a sweetening agent and certain preservatives, dyes and colorings and flavors.

In certain embodiments of the subject technology, the arylquinoline compounds are formulated as admixture with a pharmaceutically acceptable carrier, excipient or additive. In certain pharmaceutical dosage forms, the pro-drug form of the compounds may be preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

Pharmaceutical compositions containing any of the compounds of Formula (I) to Formula (III) or a pharmaceutically acceptable salt, solvate, hydrate, prodrug or metabolite thereof, may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 0.0001 mg per day to about 2 mg per day, or about 0.1 mg per day to about 100 mg per day, or about 10 mg per day to about 1000 mg per day, or from about 100 mg per day to about 10000 mg per day, or from about 5 mg per day to about 100 mg per day, to about 50 mg per day or to about 250 mg per day. In some embodiments, the total daily dose may range from about 1 mg per day to about 50 mg per day, or about 10 mg per day to about 500 mg per day. It is further recommended that children, patients over 65 years old, and those with impaired renal or hepatic function, initially receive low doses, and that the dosage be titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Alternatively, the maximum safe starting dose of the compounds of the subject technology for use in initial clinical trials in adults may be determined by following, for example, the FDA guidelines for estimating maximum safe dosage. These guidelines provide guidance for using the dosages used in animal studies to extrapolate safe dosage for use in human trials. See Guidance for Industry, Estimating the Maximum Safe Starting Dose in Initial Clinical Trials for Therapeutics in Adult Healthy Volunteers, Food and Drug Administration, Center for Drug Evaluation and Research (CDER), July 2005.

In an embodiment, the amount of compound included within therapeutically effective formulations of the subject technology is an effective amount for treating cancer or cancer metastasis by promoting apoptosis in the cancer cells. In general, a therapeutically effective amount of the present preferred compound in dosage form usually ranges from slightly less than about 0.0001 mg/kg to about 0.003 mg/kg or about 0.0025 mg/kg to about 2.5 g/kg, and in certain embodiments about 0.025 mg/kg to about 5 mg/kg or about 0.25 mg/kg to about 100 mg/kg or about 2.5 mg/kg to about 250 mg/kg or about 25 mg/kg to about 500 mg/kg or considerably more, depending upon the compound used, the condition being treated and the route of administration, although exceptions to this dosage range may be contemplated by the subject technology. In some embodiments, arylquinoline compounds of the subject technology are administered in amounts ranging from about 0.0001 mg/kg to about 1000 mg/kg.

The active compound of the subject technology, i.e., at least one of the compounds of Formula (I), (II), or (II) or a pharmaceutically acceptable salt, solvate, hydrate, prodrug or metabolite thereof, is included in the pharmaceutically acceptable carrier or diluent in an amount sufficient to deliver to a patient a therapeutically effective amount for the desired indication, without causing serious toxic effects in the patient treated.

In certain embodiments, the active compound is conveniently administered in any suitable unit dosage form, including but not limited to one containing 1 to 3000 mg, preferably 5 to 500 mg of active ingredient per unit dosage form. An oral dosage of 10-250 mg is usually convenient.

The actual dosage amount of a composition of the subject technology administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound, i.e., at least one of the compounds of Formula (I), (II), (III) or a pharmaceutically acceptable salt, solvate, hydrate, prodrug or metabolite thereof. In other embodiments, the active compound may comprise between about 1% to about 75% of the weight of the unit, or between about 5% to about 50%, for example, and any range derivable therein. In other non-limiting examples, a dose may also comprise about 0.001 microgram/kg/body weight to about 5 microgram/kg/body weight, or about 1 microgram/kg/body weight to about 50 microgram/kg/body weight, or about 20 milligram/kg/body weight to about 150 milligram/kg/body weight, or about 100 milligram/kg/body weight to about 300 milligram/kg/body weight, or about 200 milligram/kg/body weight to about 1000 milligram/kg/body weight or more per administration, and any range derivable therein. In non-limiting examples of a derivable range from the numbers listed herein, a range of about 1 microgram/kg/body weight to about 50 milligram/kg/body weight, or from about 20 microgram/kg/body weight to about 500 milligram/kg/body weight, etc., can be administered.

Route of Administration

In accordance with the methods of the subject technology, the described arylquinoline compounds of the subject technology or a pharmaceutically acceptable salt, solvate, hydrate or prodrug thereof, may be administered to a subject in a variety of forms depending on the selected route of administration, as will be understood by those skilled in the art. The active compound of the disclosure may be administered, for example, by oral, parenteral (including subcutaneous, intradermal, intramuscular, intravenous, intraperitoneal, intratumoral and intraarticular, intratumoral, transepithelial, nasal, intrapulmonary, intrathecal), buccal, sublingual, nasal, rectal, topical (including dermal, buccal, sublingual and intraocular), or transdermal administration as well as those for administration by inhalation. Parenteral administration includes intravenous, intraperitoneal, subcutaneous, intramuscular, intratumoral, transepithelial, nasal, intrapulmonary, intrathecal, rectal and topical modes of administration. Parenteral administration may be by continuous infusion over a selected period of time Alternatively, the compounds of this disclosure may be incorporated into formulations for any route of administration including for example, oral, topical and parenteral including intravenous, intramuscular, eye or ocular, intraperitoneal, intrabuccal, transdermal and in suppository form. Of course, one of ordinary skill in the art may modify the formulations within the teachings of the specification to provide numerous formulations for a particular route of administration without rendering the pharmaceutical compositions unstable or compromising their therapeutic activity. It is also well within the routineer's skill to modify the route of administration and dosage regimen of a particular compound in order to manage the pharmacokinetics of the present compounds for maximum beneficial effect to the patient.

Methods of Treatment

In an embodiment, the subject technology is directed to methods for treating cancer or treating and/or inhibiting cancer metastasis in a subject comprising administering to the subject an effective amount of a compound or composition of one or more compounds of Formula (I), (II), and/or Formula (III) and/or one or more pharmaceutically acceptable salt, solvate, hydrate, prodrug or metabolite thereof.

For example, the subject technology contemplates methods of treating various cancers and complications thereof. More particularly, the subject technology relates to methods for inhibiting the growth of benign and malignant cancer, including a malignant tumor or cancer comprising exposing the tumor to an inhibitory or therapeutically effective amount or concentration of at least one arylquinoline compound or pharmaceutically acceptable salts or pharmaceutically acceptable composition thereof. Treatment of internal malignancies such as eye or ocular cancer, rectal cancer, colon cancer, cervical cancer, prostate cancer, breast cancer, liver cancer and bladder cancer, and age-related cancer among numerous others are contemplated by the subject technology.

Accordingly, the compounds and/or compositions of the subject technology are useful for treating animals, and in particular, mammals, including humans, as patients. Thus, humans and other animals, and in particular, mammals, suffering from cancer can be treated by administering to the patient an effective amount of one or more of the arylquinoline compounds according to the subject technology, or its derivative or a pharmaceutically acceptable salt thereof, optionally in a pharmaceutically acceptable carrier or diluent, either alone, or in combination with other known pharmaceutical agents (depending upon the disease to be treated). Treatment according to the subject technology can also be by administration of the compounds and/or compositions of the subject technology in conjunction with other conventional cancer therapies, such as radiation treatment or surgery or administration of other anti-cancer agents.

In certain embodiments, the subject technology can find application in the treatment of any disease for which delivery of a therapeutic arylquinoline compound or a pharmaceutically acceptable salt, solvate, hydrate, prodrug or metabolite thereof to a cell or tissue of a subject is believed to be of therapeutic benefit. Examples of such diseases include hyperproliferative diseases and quiescent malignant diseases. In particular embodiments, the disease is a hyperproliferative disease, such as cancer of solid tissues or blood cells. Quiescent malignant diseases that can be treated by an arylquinoline compound of the subject technology or a pharmaceutically acceptable salt, solvate, hydrate, prodrug or metabolite thereof include, for example, chronic lymphocytic leukemia.

For example, a compound or composition of an arylquinoline compound of the subject technology or a pharmaceutically acceptable salt, solvate, hydrate, prodrug or metabolite thereof can be administered to treat a hyperproliferative disease. The hyperproliferative disease may be cancer, leiomyomas, adenomas, lipomas, hemangiomas, fibromas, pre-neoplastic lesions (such as adenomatous hyperplasia and prostatic intraepithelial neoplasia), carcinoma in situ, oral hairy leukoplakia, or psoriasis, for example.

The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. In certain embodiments, the cancer is ovarian cancer. In particular aspects, the cancer may be a chemo-resistant cancer, i.e., refractive forms of cancer, such as taxane-resistant or cisplatin resistant cancer.

In another aspect, the subject technology provides a method for promoting secretin of Par-4 in a cell by contacting the cell with an effective amount of an arylquinoline compound of the subject technology. In another aspect, there is provided a method for promoting apoptosis in a cancer cell by contacting the cell with an effective amount of an arylquinoline compound of the subject technology.

Combination Therapy

The active compounds of the subject technology, i.e., one or more compounds of Formula (I) to (III) and/or one or more pharmaceutically acceptable salt, solvate, hydrate, prodrug or metabolite thereof can also be mixed with other active materials that do not impair the desired action, or with materials that supplement the desired action, such as chemotherapeutic agents, NF-κB inhibitors, other anticancer agents, and in certain instances depending upon the desired therapy or target, antibiotics, antifungals, antiinflammatories, antiviral compounds or other agents having a distinct pharmacological effect.

The methods and compositions of the subject technology further provide combination therapies which can enhance the therapeutic or protective effect of the compounds of the subject technology, and/or increase the therapeutic effect of another anti-cancer. Therapeutic and prophylactic methods and compositions can be provided in a combined amount effective to achieve the desired effect, such as the killing of a cancer cell and/or the inhibition of cancer metastasis. This process may involve contacting the cells with, for example, a therapeutic nucleic acid, such as a chemotherapeutic agent or an inhibitor of gene expression, as a second therapy. A tissue, tumor, or cell can be contacted with the compounds or compositions of the subject technology and one or more additional anti-cancer treatment. For example, an additional anticancer treatment may include a chemotherapeutic agent, an NF-κB inhibitor, an anti-hormonal agent, radiotherapy, surgical therapy, or immunotherapy.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-I 1); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristine, vinblastine and methotrexate and pharmaceutically acceptable salts, acids or derivatives of any of the above.

Examples of nf-κb inhibitors include 9-methylstreptimidone, n-stearoyl phytosphingosine, 2-(1,8-naphthyridin-2-yl)-phenol, 5-aminosalicylic acid, cape (caffeic acid phenethylester), diethylmaleate, ethyl 3,4-dihydroxycinnamate, helenalin, nf-κb activation inhibitor ii, nfκb activation inhibitor iii, glucocorticoid receptor modulator, cpda, aspirin, ppm-18, pyrrolidinedithiocarbamic acid ammonium salt, rocaglamide, sodium salicylate, andrographolide, (±)4-hydroxynon-2-enal, ps-1145 dihydrochloride, pioglitazone, sulindac sulfide, isohelenin, diethyldithiocarbamic acid sodium salt trihydrate, curcumin (synthetic), trichodion (which can be purchased, e.g., from Santa Cruz Biotechnology, Inc. Dallas, Tex.).

Also included in the formulations may be anti-hormonal agents that act to regulate or inhibit hormone action on tumors such as anti-estrogens and selective estrogen receptor modulators (SERMs), including, for example, tamoxifen, raloxifene, droloxifene, A-hydroxytamoxifen, trioxifene, keoxifene, LYI 17018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analogue); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

In an embodiment, a therapeutic formulation or composition set forth herein, which comprises one or more compounds of Formula (I) to Formula (III) and/or one or more pharmaceutically acceptable salt, solvate, hydrate, prodrug or metabolite thereof, may be administered before, during, after or in various combinations relative to a second anti-cancer treatment. The administrations may be in intervals ranging from concurrently to minutes to days to weeks. In embodiments where the arylquinoline containing composition is provided to a patient separately from an additional anti-cancer agent, one would generally ensure that a significant period of time did not expire between the time of each delivery, such that the two agents would still be able to exert an advantageously combined effect on the patient. In such instances, it is contemplated that one may provide a patient with the inhibitor of gene expression therapy and the anti-cancer therapy within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

Within a single day (24-hour period), the patient may be given one or multiple administrations of the agent(s). Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Administration of any compound or therapy of the subject technology to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as radiation and surgical intervention, may be applied in combination with the described therapy.

In specific aspects, it is contemplated that a standard therapy will include chemotherapy, radiotherapy, immunotherapy, surgical therapy or gene therapy and may be employed in combination with the combination therapy described herein.

Articles of Manufacture

In another embodiment of the disclosure, an article of manufacture, or "kit", containing materials useful for the treatment of the diseases and disorders described above is provided. In one embodiment, the kit comprises a container comprising at least one compound of Formula (I)-(III), and/or one or more pharmaceutically acceptable salt, solvate, hydrate, prodrug or metabolite thereof.

The kit may further comprise a label or package-insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula (I)-(III) or a formulation thereof which is effective for treating the condition and may have a sterile access port (for example, the container may be an intravenous solution bag or a vial having a stopper pierceable by a hypodermic injection needle). At least one active agent in the composition is a compound of Formula (I)-(III). The label or package insert indicates that the composition is used for treating the condition of choice, such as cancer.

In an embodiment, the kit includes two separate pharmaceutical compositions: one containing a compound of the subject technology, and a second pharmaceutical compound. In another embodiment, an assay or diagnostic kit includes a labeled compound of the subject technology and one or more reagents necessary for detecting the labeled compound upon binding to its target in-vivo or in-vitro. In a related embodiment, the kit includes a package insert that describes the steps necessary for carrying out the detection assay.

In another embodiment, a kit of the disclosure further comprises a needle or syringe, preferably packaged in sterile form, for injecting the composition, and/or a packaged alcohol pad. Instructions are optionally included for administration of arylquinoline compounds by a clinician or by the patient.

Diagnostic Methods and Diagnostic Probes

Another aspect of the subject technology provides compounds having general formulas (I)-(III) with a linker moiety (hydrophobic linkers, hydrophilic linkers, photo-cleavable linkers, redox reaction-cleavable linkers), wherein the linker moiety is covalently bonded to a label molecule (a label could be a fluorophor, biotin, different polymer beads and different reactive groups). An exemplary biotinylated analog is depicted in FIG. 1.

The compounds of the subject technology when biotinylated provide suitable means for non-radioactive detection of target molecules that may play a role in apoptosis induction in cells. Therefore, another aspect of the subject technology relates to the use of biotinylated arylquinoline compounds as a diagnostic reagent for detecting or monitoring the presence or levels of vimentin in a complex protein sample. A complex protein sample contains multiple proteins, and may additionally contain other contaminants. Non-limiting examples of a complex protein sample include tumor tissues, biopsy, serum and cell extracts.

In one embodiment, the subject technology relates to a method of detecting, monitoring or analyzing the levels of vimentin in a complex protein sample, said method comprising adding a labeled compound of Formula (I)-(III) to said complex protein mixture under conditions whereby said labeled compound covalently conjugates to vimentin; isolating the conjugated vimentin by a suitable affinity-based separation method, removing unbound proteins, detecting the level of vimentin following the separation. In a related embodiment, the detection can be accomplished by measuring a fluorescence signal emitted from the compound of Formula (I)-(III). In another related embodiment, the detection can be accomplished by measuring a fluorescence signal emitted from a label bound via a linker to the compound of Formula (I)-(III). The detection step can also be accomplished using various analytical procedures that known to the artisan for separating and analyzing complex protein mixtures. These analytical procedures include chromatographic methods such as HPLC, FPLC, ion exchange, size exclusion, mass spectrometry, and the like.

The linker moiety that can be used to attach a detectable label to the compounds of the subject technology can be any of the linkers shown in FIG. 1. Alternatively, the linker moiety comprises a repeating alkyleneoxy structure (polyethylene glycols, or "PEG"). Thus, one of skill in the art can select the linker moiety of the compounds of the subject technology in order to provide additional specificity of them for vimentin.

In an embodiment, it is desirable to have a detectable label associated with a compound of the subject technology to allow the compound-vimentin complex to be captured and washed free of other components of the reaction mixture. The label will generally be under about 1 kDa. Biotin is a conventional label or ligand, particularly analogs such as dethiobiotin and deiminobiotin, which can be readily displaced from streptavidin by biotin. However, any small molecule will suffice that can be captured and released under convenient conditions.

Affinity purification of biological molecules, for example proteins, is known in the art and allows the purification of molecules by exploiting the binding affinity of the target molecule for a molecular binding partner. Examples of affinity purification methods are fusion tag protein purification, avidin-biotin system, pull-down assay and the like.

Drug Screening Assays

In another aspect, the subject technology provides assays for screening test compounds that interfere with vimentin binding to PAR-4 or which cause release of vimentin-bound PAR-4. In a typical assay, cells, such as HEL cells, are seeded onto an appropriate support, such as 60-mm plates containing supplemented growth medium (e.g., supplemented with 0.1% serum) at a desired confluency, such as 40-70% confluency, and treated with the test compound (e.g., 500 nM) or control vehicle. The cells are allowed to grow for a period of time, such as 24 hours, after which the conditioned medium (CM) is concentrated (e.g., concentrated 30× to 100 μl using Millipore tubes (Amicon Ultra centrifugal filters, Ultracel-10K) by 15 min centrifugation at 4500 rpm). The concentrated CM is then subjected to co-immunoprecipitation using detectably labeled PAR-4 and vimentin antibodies in the presence of various concentrations of purified PAR-4 and the precipitated proteins are resolved by SDS-PAGE and analyzed by Western blot analysis. The amount of immunoprecipitated PAR-4-vimentin complex is compared to that of control samples. For example, chemiluminescent signals may be quantified in the BIO-RAD Molecular Imager ChemiDoc XRS+Imaging system using Quantity One software. Induction of Par-4 secretion by the test drug (e.g., 500 nM), as judged by this Western blot analysis procedure, will indicate dissociation of Par-4 from vimentin. Additionally, experiments can be undertaken to determine whether the test compound disrupts the interaction between vimentin and Par-4 using any test drug that shows elevated secretion of Par-4 by Western blot analysis or other such assay. For such experiments, cells may be treated with the test drug (e.g., 500 nM) or vehicle for an appropriate period of time, such as 24 hours, and then cell lysates are prepared and subjected to immunoprecipitation using an appropriate amount of a Par-4 antibody, vimentin antibody or control IgG antibody by using any standard immunoprecipitation procedure. Following immunosuppression, the complexes are resolved, preferably by Western blot analysis as described above. If the drug inhibits the binding of Par-4 to vimentin, it will be reflected in the lack of co-immunoprecipitation of Par-4 with the vimentin antibody, and co-immunoprecipitation of vimentin with the Par-4 antibody.

EXAMPLES

The following examples are intended to further illustrate certain preferred embodiments of the disclosure and are not limiting in nature. Those skilled in the art will recognize, or be able to ascertain, using no more than routine experimentation, numerous equivalents to the specific substances and procedures described herein.

Materials and Methods

The following materials and methods were used for the experiments described herein.

Chemistry: Nutlin-3a, an inhibitor of MDM2 that is reported to bind directly to MDM2, release, stabilize and activate p53, was acquired from Cayman Chemical Company. Brefeldin A, N-benzyloxycarbonyl-Val-Ala-Asp(O-Me) fluoromethyl ketone (zVAD-fmk) and other chemicals were purchased from Sigma Aldrich or Fisher Scientific or were synthesized according to literature procedures. The synthesis of Arylquin 1, which utilized 4-(N,N-dimethylamino)-2-aminobenzaldehyde in a Friedländer condensation with 2-fluorophenylacetontrile (see Zhang, W., et al. *ACS Chem Biol* 8, 796-803 (2013)), and other heterocyclic families is described in the synthesis section below. The condensation of 2-amino-4-(N,N-dimethylamino)benzaldehyde with 2-(2-fluorophenyl)acetyl chloride secured 7-(dimethylamino)-3-(2-fluorophenyl)quinolin-2(1H)-one, and treatment with Lawesson's reagent (see Goswami, A., et al. *Cancer Res* 68, 6190-6198 (2008)) provided 7-(dimethylamino)-3-(2-fluorophenyl)quinoline-2(1H)-thione. S-alkylation of this intermediate with (+)-biotinyl-iodoacetamidyl-3,6-dioxaoctanediamine led to biotinylated Arylquin 9 (see the synthesis section below). Solvents were used from commercial vendors without further purification unless otherwise noted. Nuclear magnetic resonance spectra were determined on a Varian instrument ($^1$H, 400 MHz; $^{13}$C, 100 Mz). High resolution electrospray ionization (ESI) mass spectra were recorded on a LTQ-Orbitrap Velos mass spectrometer (Thermo Fisher Scientific, Waltham, Mass., USA). The FT resolution was set at 100,000 (at 400 m/z). Samples were introduced through direct infusion using a syringe pump with a flow rate of 5 µL/min. MALDI mass spectra were obtained on a Bruker Utraflexstreme time-of-flight mass spectrometer (Billerica, Mass.), using DHB (2,5-dihydroxybenzoic acid) matrix. Purity of compounds was established by combustion analyses by Atlantic Microlabs, Inc., Norcross, Ga. Compounds were chromatographed on preparative layer Merck silica gel F254 unless otherwise indicated.

Cells and plasmids: Human lung cancer cells H1299, HOP92, A549, H460, mouse lung cancer cells LLC1, human prostate cancer cells LNCaP, DU145, PC-3, and primary human lung fibroblast cells HEL and epithelial cells HBEC and BEAS-2B were from ATCC, MD; normal human prostate epithelial cells PrE and human prostate stromal cells PrS were from Lonza Inc., Allendale, N.J. KP7B cells were from Tyler Jacks, MIT, MA. PC-3 derivatives PC-3 MM2 were from Sue-Hwa Lin, M.D. Anderson Cancer Center, Houston, Tex. Par-4$^{+/+}$ and Par-4$^{-/-}$ MEFs were derived from wild type and Par-4-null C57BL/6 mice generated by Taconic. See Eckes, B., et al. *J Cell Sci* 113, 2455-2462 (2000). Vimentin-null (Vim$^{-/-}$) and wild type MEFs, as well as vimentin-expressing (Vim$^+$) and vimentin-deficient (Vim$^-$) SW13 cells were from Anthony Brown (Ohio State University).

Antibodies and siRNA duplexes: Par-4 (R334), Col1A1 (H-197), Vimentin (H-84) for Western blot; Vimentin (RV202) for ICC and immunoprecipitation; GRP78 (N20), Col1A1 (H-197), p53 (DO-1) and pan-cytokeratin (C1) antibodies were from Santa Cruz Biotechnology, Inc. Active caspase 3 antibody (Asp175) (5A1E) and p53 antibody (1C12) were from Cell Signaling. The β-actin antibody was from Sigma Chemical Corp.

Pull down experiments: To identify the target protein for compound Arylquin 1, pull-down experiments were performed as described previously. See Bargagna-Mohan, P., et al. J Biol Chem 285, 7657-7669 (2010). MEFs or HEL cells (grown to confluence in 15 cm plates) were lysed in 50 ml lysis buffer (40 mM Hepes, pH 7.8; 140 mM NaCl; 10 mM NaF; 10% Glycerol, 1 mM EDTA; 1% Triton 100), and the lysates were pre-cleared at 4° C. for 1 h with 100 µL streptavidin beads (Novagen, Strep-Tactin Superflow Agarose). Binding reactions were performed by incubating the pre-cleared cell lysates with 50 µL beads±25 µg of biotinylated Arylquin 1 at 4° C. for 2 h. The beads were then washed four times with buffer (40 mM Hepes, pH 7.8; 140 mM NaCl; 10 mM NaF; 10% Glycerol, 1 mM EDTA), and bound protein was eluted with 50 µL of 2.5 mM Biotin/PBS. Eluted proteins were resolved by SDS-PAGE and Coomassie blue staining.

Co-Immunoprecipitation and Western blot analysis: Protein extracted from cell lysates was filtered, pre-cleared with 25 µL (bed volume) of protein G-Sepharose beads and immunoprecipitated with 1 µg of respective antibodies. The eluted proteins were resolved by SDS-PAGE, and subjected to Western blot analysis as described.

Apoptosis assays: Apoptotic nuclei were identified by immunocytochemical (ICC) analysis for active caspase-3, and nuclei were revealed by 4, 6-diamidino-2-phenylindole (DAPI) staining. See Hebbar, N., Wang, C. & Rangnekar, V. M. *J Cell Phys* 227, 3715-3721 (2012) and Shrestha-Bhattarai, T., Hebbar, N. & Rangnekar, V. M. *Cancer Cell* 24, 3-5 (2013). A total of three independent experiments were performed; and approximately 500 cells were scored in each experiment for apoptosis under a fluorescent microscope. Cell surface GRP78 expression on the cancer cell surface was quantified by FACS analysis in the Flow Cytometry Shared Resource Facility, Markey Cancer Center as previously described. See Hebbar, N., Wang, C. & Rangnekar, V. M. *J Cell Phys* 227, 3715-3721 (2012).

Animal experiments: C57BL/6 mice were injected via the intraperitoneal route with Arylquin 1 (10 mg/kg body weight) or corn oil vehicle, and whole-blood samples were collected 24 h later. Serum was separated from the blood samples, heated at 56° C. to inactivate complement. Aliquots of the mouse serum samples were added to the growth medium (final 20% mouse serum) of normal and cancer cells in culture and tested for induction of ex vivo apoptosis in cancer cells. All animal procedures were performed with University of Kentucky IACUC approval.

Computational modeling: Molecular modeling of vimentin binding with Arylquin 1 and the analogs was performed by using the previously reported computational protocol. Ee Hamza, A. et al., *J Chem Inform Model* 54, 1166-1173 (2014) and Hamza, A. & Zhan, C.-G. *J Phys Chem B* 113, 2896-2908 (2009). Briefly, each ligand was docked into the binding cavity and the resulting poses were refined by molecular dynamics (MD)-simulations. The most favorable binding mode (with the lowest binding free energy), which was identified in the docking procedure, was subjected to an MD simulation for 1 ns at 298 K and used in binding free energy calculations.

Statistical analysis: All experiments were performed in triplicate to verify the reproducibility of the findings. The results show a mean of at least 3 experiments±Standard Deviation (s.d.). Statistical analyses were carried out with Statistical Analysis System software (SAS Institute, Cary, N.C.) and P values were calculated using the Student t test. The effect of interaction between two different treatments was analyzed using a two-way ANOVA model with data normality and equality of variance assumptions.

Synthesis of Compounds

FIG. 1 illustrates a general scheme for the synthesis of arylquins and depiction of Arylquin 1. Reagents: a, arylacetonitrile, tert-BuOK, DMF, 90° C., 3-4 h; b, 2(2'-fluorophenyl)acetyl chloride, Et$_3$N, reflux 2 h and then K$_2$CO$_3$, DMF, 90° C., 4 h; c, 2,4-bis(4-methoxyphenyl)-2,4-dithioxo-1,3,2,4-dithiadiphosphetane (Lawesson's reagent), dioxane, reflux 5 h; d, (+)-biotinyl-iodoacetamidyl-3,6-dioxaoctanediamine, K$_2$CO$_3$, DMF, 12 h; e, POCl3, reflux, 3 h; f, Zn, CH$_3$CO$_2$H, 75° C., 1 h.

General Procedure for the Synthesis of Arylquins. To a solution of 2.38 mmol (1.3 equiv) of the appropriate benzyl cyanide in 3 mL of anhydrous DMF at 0° C. was added 2.38 mmol (1.3 equiv) of potassium tert-butoxide. The mixture was stirred for 15 min, and 1.83 mmol of appropriate 2-aminobenzaldehyde dissolved in 1 mL of anhydrous DMF was added dropwise at 0° C. The mixture was warmed to 25° C. and stirred for 3-4 h at 90° C. After cooling the mixture was quenched by pouring into water to afford a precipitate that was collected and purified by recrystallization and/or chromatography as noted for individual compounds described below.

3-(2-Fluorophenyl)-N$^7$,N$^7$-dimethylquinoline-2,7-diamine (Arylquin-1). Purified by recrystallization from ethanol: Yield 83%, mp 159-160° C. $^1$H NMR (DMSO-d6): δ 7.63 (s, 1H), 7.50-7.41 (m, 3H), 7.33-7.28 (m, 2H), 6.86 (dd, 1H, J1=8.8 Hz, J2=2.8 Hz), 6.61 (d, 1H, J=2.8 Hz), 5.67 (s, 2H, NH2), 3.00 (s, 6H). 13C NMR (DMSO-d6): δ 160.09 (d, J=242.6 Hz), 156.25, 151.88, 149.72, 137.78, 132.37 (d, J=3.1 Hz), 130.26 (d, J=7.6 Hz), 128.58, 125.92 (d, J=16.0 Hz), 125.27 (d, J=3.8 Hz), 116.47 (d, J=22.1 Hz), 115.63, 114.33, 111.55, 104.16, 40.51 (two C). HRMS (ESI) calcd for $C_{17}H_{17}FN_3$ [MH+]: 282.14010. Found: 282.14056. Anal. Calcd for $C_{17}H_{16}FN_3$: C, 72.58; H, 5.73. Found: C, 72.52; H, 5.79.

3-(3-Fluorophenyl)-$N^7,N^7$-dimethylquinoline-2,7-diamine (Arylquin 2) Purified by recrystallization from ethanol: Yield 84%, mp 147-148° C. $^1$H NMR (DMSO-d6): δ 7.68 (s, 1H), 7.53-7.48 (m, 2H), 7.34-7.30 (m, 2H), 7.23-7.18 (m, 1H), 6.86 (dd, 1H, J1=8.8 Hz, J2=2.4 Hz), 6.61 (d, 1H, J=2.8 Hz), 5.69 (s, 2H, NH2), 3.00 (s, 6H). 13C NMR (DMSO-d6): δ 162.78 (d, J=242.9 Hz), 155.85, 151.81, 149.48, 141.22 (d, J=7.6 Hz), 137.03, 131.18 (d, J=8.4 Hz), 128.69, 125.27 (d, J=2.3 Hz), 119.17 (d, J=2.3 Hz), 116.07, 115.93 (d, J=21.3 Hz), 114.45 (d, J=20.5 Hz), 111.63, 104.07, 40.48 (two C). HRMS (ESI) calcd for $C_{17}H_{17}FN_3$ [MH+]: 282.14010. Found: 282.14095. Anal. Calcd for $C_{17}H_{16}FN_3$: C, 72.58; H, 5.73. Found: C, 72.54; H, 5.64.

3-(4-Fluorophenyl)-N,N-dimethylquinoline-2,7-damine (Arylquin 3) Purified by recrystallization from acetonitrile: Yield 91%, mp 155-156° C. 1H NMR (DMSO-d6): δ 7.62 (s, 1H), 7.53-7.48 (m, 3H), 7.31-7.27 (m, 2H), 6.85 (dd, 1H, J1=9.2 Hz, J2=2.8 Hz), 6.61 (d, 1H, J=2.4 Hz), 5.74 (s, 2H, NH2), 2.99 (s, 6H). $^{13}$C NMR (DMSO-d6): δ 161.91 (d, J=242.1 Hz), 156.13, 151.68, 149.34, 136.78, 135.11, 131.22 (d, J=8.3 Hz, two C), 128.55, 119.53, 116.16, 116.08 (d, J=21.2 Hz, two C), 111.56, 104.16, 40.51 (two C). HRMS (ESI) calcd for C17H17FN3 [MH+]: 282.14010. Found: 282.14085. Anal. Calcd for $C_{17}H_{16}FN_3$: C, 72.58; H, 5.73. Found: C, 72.31; H, 5.58.

7-(Dimethylamino)-3-(2-fluorophenyl)quinolin-2(1H)-one (Arylquin 4) To a mixture of 1.00 g (6.09 mmol) of 2-amino-4-(dimethylamino)benzaldehyde 15 and 0.68 g (6.70 mmol, 1.1 equiv) of triethylamine in dichloromethane (10 mL), we added 1.05 g (6.09 mmol, 1 equiv) of 2-(2-fluorophenyl)acetyl chloride dropwise over a 15 min period. The mixture was stirred at reflux for 2 h. After cooling to the room temperature, the mixture was washed with 30 mL of water, and the organic layer was separated, dried over anhydrous MgSO4 and concentrated under reduced pressure. The crude residue, obtained after concentration, was dissolved in DMF (10 mL) followed by addition of 1.01 g (7.31 mmol, 1.2 equiv) of $K_2CO_3$. The resulting mixture was stirred at 90° C. for 4 h, poured into water and a precipitate was collected by filtration and dried in vacuum. The product was purified by recrystallization from acetonitrile to provide 1.38 g (80%) of 7-(dimethylamino)-3-(2-fluorophenyl)quinolin-2(1H)-one (Arylquin 4) as a pale yellow solid: mp 247-248° C. $^1$H NMR (DMSO-d6): δ 11.52 (s, 1H), 7.79 (s, 1H), 7.51-7.47 (m, 2H), 7.40-7.35 (m, 1H), 7.25-7.20 (m, 2H), 6.69 (dd, 1H, J1=8.8 Hz, J2=2.4 Hz), 6.48 (d, 1H, J=2.4 Hz), 3.00 (s, 6H). $^{13}$C NMR (DMSO-d6): δ 160.88, 159.75 (d, J=244.3 Hz), 151.75, 140.74, 139.69 (d, J=1.5 Hz), 131.89 (d, J=3.8 Hz), 129.18 (d, J=7.5 Hz), 128.97, 125.03 (d, J=15.2 Hz), 123.89 (d, J=3.0 Hz), 121.09, 115.32 (d, J=22.0 Hz), 109.97, 108.65, 94.74, 39.76 (two C). HRMS (ESI) calcd for $C_{17}H_{16}FN_2O$ [MH+]: 283.12412. Found: 283.12473. Anal. Calcd for $C_{17}H_{15}FN_2O$: C, 72.32; H, 5.36. Found: C, 72.19; H, 5.41.

7-(Dimethylamino)-3-(2-fluorophenyl)quinoline-2(1H)-thione (Arylquin 5) A mixture of 500 mg (1.77 mmol, 1 equiv) of 7-(dimethylamino)-3-(2-fluorophenyl)quinolin-2(1H)-one (Arylquin 4) and 716 mg (1.77 mmol, 1 equiv) of Lawesson's reagent 16 in anhydrous 1,4-dioxane (10 mL) was stirred at reflux for 5 h. After cooling, a precipitate was collected, washed with 10% aqueous NaOH solution (5 mL) and water and dried in vacuum. The product was purified by recrystallization from acetonitrile to provide 350 mg (66%) of 7-(dimethylamino)-3-(2-fluorophenyl)quinoline-2(1H)-thione (Arylquin 5) as a pale yellow solid: mp 251-253° C. $^1$H NMR (DMSO-d6): δ 13.24 (s, 1H), 7.75 (s, 1H), 7.58 (d, 1H, J=9.2 Hz), 7.41-7.37 (m, 2H), 7.23-7.18 (m, 2H), 6.91 (dd, 1H, J1=8.8 Hz, J2=1.8 Hz), 6.82 (d, 1H, J=1.8 Hz), 3.04 (s, 6H). $^{13}$C NMR (DMSO-d6): δ 179.45, 159.51 (d, J=242.9 Hz), 152.16, 141.29, 135.82, 132.20 (d, J=3.2 Hz), 129.87, 129.29 (d, J=8.4 Hz), 128.81, 127.89 (d, J=15.2 Hz), 123.75 (d, J=3.1 Hz), 115.16 (d, J=22.0 Hz), 113.76, 111.61, 94.50, 39.77 (two C). HRMS (ESI) calcd for $C_{17}H_{16}FN_2S$ [MH+]: 299.10127. Found: 299.10176. Anal. Calcd for $C_{17}H_{15}FN_2S$: C, 68.43; H, 5.07. Found: C, 68.23; H, 5.18.

3-(2-Fluorophenyl)-N,N-dimethylquinolin-7-amine (Arylquin 6) A mixture of 500 mg (1.77 mmol, 1 equiv) of 7-(dimethylamino)-3-(2-fluorophenyl)quinolin-2(1H)-one (Arylquin 4) and 5 mL of phosphoryl chloride (POCl3) was refluxed for 3 h. The mixture was poured on to ice and neutralized with 10% aqueous sodium carbonate solution at 0° C. A precipitate was collected by filtration, dried in vacuo and purified by chromatography using 1:5 ethylacetate-hexane (Rf=0.25) to afford 415 mg (78%) of 2-chloro-3-(2-fluorophenyl)-N,N-dimethylquinolin-7-amine as a pale yellow solid: mp 170-172° C. $^1$H NMR (DMSO-d6): δ 8.20 (s, 1H), 7.83 (d, 1H, J=9.2 Hz), 7.54-7.46 (m, 2H), 7.36-7.29 (m, 3H), 6.95 (d, 1H, J=2.4 Hz), 3.09 (s, 6H). 13C NMR (DMSO-d6): δ 159.36 (d, J=243.6 Hz), 151.97, 148.83, 148.76, 139.50, 132.05 (d, J=3.0 Hz), 130.50 (d, J=8.4 Hz), 128.59, 125.54 (d, J=16.0 Hz), 125.51 (d, J=3.8 Hz), 122.92, 118.79, 116.87, 115.52 (d, J=21.2 Hz), 104.18, 39.86 (two C). HRMS (ESI) calcd for $C_{17}H_{14}ClFN_2$ [MH+]: 301.09023. Found: 301.08961. Anal. Calcd for C17H14ClFN2: C, 67.89; H, 4.69. Found: C, 67.76; H, 4.52. To a solution of 200 mg (0.66 mmol) of 2-chloro-3-(2-fluorophenyl)-N,N-dimethylquinolin-7-amine in 9 mL of glacial acetic acid and 0.7 mL of water at 75° C. was added 174 mg (2.66 mmol, 4 equiv) of zinc powder. After 1 h, the mixture was quenched by addition of 40% aqueous sodium hydroxide solution to a pH of 9-10. The solution was extracted with dichloromethane and the organic layer was washed with water, dried over anhydrous MgSO4 and concentrated under reduced pressure. The product was purified by chromatography using 1:2 ethylacetate-hexane to afford 98 mg (55%) of 3-(2-fluorophenyl)-N,N-dimethylquinolin-7-amine (Arylquin 6) as a pale yellow solid: mp 142-144° C. 1H NMR (DMSO-d6): δ 8.86 (s, 1H), 8.30 (s, 1H), 7.84 (d, 1H, J=8.8 Hz), 7.70-7.60 (m, 1H), 7.48-7.43 (m, 1H), 7.39-7.32 (m, 3H), 7.02 (d, 1H, J=2.4 Hz), 3.09 (s, 6H). 13C NMR (DMSO-d6): δ 159.33 (d, J=244.3 Hz), 151.28, 150.24 (d, J=3.8 Hz), 148.80, 134.71 (d, J=3.0 Hz), 130.73 (d, J=3.0 Hz), 129.61 (d, J=8.4 Hz), 128.90, 125.75 (d, J=13.6 Hz), 125.16 (d, J=3.0 Hz), 123.78, 119.68, 116.78, 116.19 (d, J=22.0 Hz), 105.53, 39.99 (two C). HRMS (ESI) calcd for C17H15FN2 [MH+]: 267.12920. Found: 267.12839. Anal. Calcd for $C_{17}H_{15}FN_2$: C, 76.67; H, 5.68. Found: C, 76.53; H, 5.52.

$N^7,N^7$-Dimethyl-3-phenylquinoline-2,7-diamine (Arylquin 7) Purified by chromatography on silica gel using 1:10 methanol-dichloromethane (Rf=0.48): Yield 83%, mp 123-125° C. $^1$H NMR (DMSO-d6): δ 7.64 (s, 1H), 7.52-7.46 (m, 5H), 7.41-7.36 (m, 1H), 6.86 (dd, 1H, J1=8.6 Hz, J2=2.6 Hz), 6.62 (d, 1H, J=2.4 Hz), 3.00 (s, 6H). $^{13}$C NMR (DMSO-d6): δ 155.55, 151.25, 148.68, 138.28, 136.34, 128.88 (two C), 128.66 (two C), 128.15, 127.29, 120.05, 115.77, 111.15, 103.63, 40.07 (two C). HRMS (ESI) calcd for C17H18N3 [MH+]: 264.14952. Found: 264.15024. Anal. Calcd for $C_{17}H_{17}N_3$: C, 77.54; H, 6.51. Found: C, 77.27; H, 6.43.

3-(2-Fluorophenyl)quinolin-2-amine (Arylquin 8) Purified by chromatography on silica gel using 1:10 methanol-dichloromethane (Rf=0.55): Yield 79%, mp 152-153° C. $^1$H NMR (DMSO-d6): δ 7.87 (s, 1H), 7.70 (d, 1H, J=8.0 Hz), 7.55-7.44 (m, 4H), 7.37-7.32 (m, 2H), 7.22-7.18 (m, 1H), 6.03 (s, 2H, NH2). 13C NMR (DMSO-d6): δ 159.56 (d, J=243.6 Hz), 155.85, 147.59, 137.86, 131.77 (d, J=3.3 Hz), 130.36 (d, J=8.0 Hz), 129.52, 127.65, 124.95, 124.90, 124.77 (d, J=16.1 Hz), 122.80, 121.59, 118.76, 116.11 (d, J=22.2 Hz). HRMS (ESI) calcd for $C_{15}H_{12}FN_2$ [MH+]: 239.09790. Found: 239.09831. Anal. Calcd for $C_{15}H_{11}FN_2$: C, 75.62; H, 4.65. Found: C, 72.39; H, 4.71.

N-(2-(2-(2-(2-(7-(dimethylamino)-3-(2-fluorophenyl) quinolin-2-ylthio)acetamido)ethoxy)ethoxy)ethyl)-5-(2-oxohexahydro-1H-thieno[3,4-d]imidazol-4-yl)pentanamide (Biotinylated Arylquin 9). To a solution of 28 mg (0.092 mmol) of 7-(dimethylamino)-3-(2-fluorophenyl)quinoline-2 (1H)-thione in 1 mL of DMF was added 15 mg (0.11 mmol, 1.2 equiv) of K2CO3 and 50 mg (0.092 mmol) of (+)-biotinyl-iodoacetamidyl-3,6-dioxaoctanediamine. The mixture was stirred for 12 h at 25° C., poured into water, extracted with dichloromethane, dried over anhydrous MgSO$_4$ and concentrated under reduced pressure. The product was purified by chromatography 1:10 methanol-dichloromethane (Rf=0.25) to afford 29 mg (44%) of biotinylated Arylquin 9 as a pale yellow solid: $^1$H NMR (DMSO-d6): δ 8.03 (t, 1H, J=4.8 Hz), 7.70 (s, 1H), 7.59 (d, 1H, J=8.8 Hz), 7.44-7.35 (m, 2H), 7.23-7.14 (m, 2H), 7.08 (dd, 1H, J1=8.8 Hz, J2=2.8 Hz), 7.00 (d, 1H, J=2.4 Hz), 6.42 (t, 1H, J=4.8 Hz), 6.07 (br s, 1H), 5.07 (br s, 1H), 4.43-4.40 (m, 1H), 4.25-4.22 (m, 1H), 3.92 (s, 2H), 3.48-3.46 (m, 2H), 3.43-3.39 (m, 2H), 3.32-3.28 (m, 6H), 3.21-3.19 (m, 2H), 3.12 (s, 6H), 3.09-3.05 (m, 1H), 2.84 (dd, 1H, J1=12.8 Hz, J2=4.8 Hz), 2.66 (d, 1H, J=12.8 Hz), 2.14 (t, 2H, J=8.0 Hz), 1.68-1.56 (m, 4H), 1.41-1.36 (m, 2H). 13C NMR (DMSO-d6): δ 173.32, 170.59, 163.70, 160.28, 157.28, 152.12, 149.30, 136.68, 132.41 (d, J=2.1 Hz), 130.71 (d, J=8.0 Hz), 128.67, 125.27 (d, J=16.1 Hz), 124.45 (d, J=3.4 Hz), 123.95, 118.38, 116.14 (d, J=22.2 Hz), 115.46, 107.65, 105.43, 70.26, 70.15, 70.00, 69.92, 61.94, 60.29, 55.59, 40.72, 39.75, 39.23, 36.08, 33.82, 29.92, 28.31, 28.26, 27.72. MALDI-TOF MS calcd for $C_{35}H_{46}FN_6O_5S_2$ [MH+]: 713.2955. Found: 713.2936.

Testing of Arylquinolines for Promoting Secretion of Par-4

To identify Par-4 secretagogues, we synthesized and screened 3-arylquinolines as well as related quinolones and quinothiolones for the secretion of Par-4 protein from normal fibroblasts under conditions that are not toxic to the cells.

Nutlin-3a, originally developed as an MDM2 inhibitor, stimulated Par-4 secretion at micromolar levels in mouse embryonic fibroblast (MEF) cells. The presence of halogen substituents on an aromatic ring, two aromatic rings separated by a two-atom spacer (i.e., 1,2-diphenylethane subunit) and a nitrogen-containing heterocycle (i.e., an imidazole subunit) in Nutlin-3a enabled us to screen an in-house library that possessed similar features, namely halogenated aromatic rings separated by two-atom spacers (i.e., 1,2-diphenylethene or stilbene subunits) and nitrogen-containing heterocycles. Specifically, we focused on halogenated 3-arylquinolines, 3-arylquinolones, and 3-arylthioquinolones, which possessed stilbene subunits and nitrogen-containing heterocyclic rings imbedded within their structures. We screened representative members of each of these heterocyclic families on a compound-by-compound basis for the secretion of Par-4 protein from normal mouse fibroblasts under conditions that were not toxic to the cells. Initial expectations were that these heterocycles would serve as Nutlin-3a surrogates and inhibit MDM2, but studies reported herein established a completely different mechanism of action, reflecting that the structural dissimilarities between these heterocycles and Nutlin-3a outweighed the similarities that led to their initial selection for screening.

Within this library of compounds, the fluorinated 3-arylquinolines proved particularly promising in promoting Par-4 secretion. Structure-activity studies defined that 3-arylquinolines, such as Arylquin 1, was most active as the leading member of a new class of "small-molecule" Par-4 secretagogues. Arylquin 1 produced a dose-dependent secretion in MEF cells. Arylquin 1 also induced robust secretion of Par-4 in normal/immortalized human cells, but failed to induce the secretion of Par-4 in a panel of lung tumor cells. By contrast, prostate cancer cells showed induction of Par-4 secretion with Arylquin 1 relative to vehicle control. Consistent with previous studies, Brefeldin A, which blocked anterograde endoplasmic reticulum-Golgi traffic, inhibited basal as well as Arylquin 1-inducible Par-4 secretion. See Hebbar, N., Wang, C. & Rangnekar, V. M. *J Cell Phys* 227, 3715-3721 (2012). These findings indicated that Arylquin 1 regulated Par-4 secretion via the classical secretory pathway.

To identify the molecular target responsible for the observed Par-4 secretory activity, we synthesized a biotinylated Arylquin 9. Biotinylated Arylquin 9 was confirmed experimentally to retain Par-4 secretory properties and was then used in pull-down experiments for potential protein targets in mouse fibroblasts (MEFs) and human fibroblasts (HEL).

We identified vimentin, a cytoskeletal intermediate filament protein, as its principal target. The binding of Par-4 to vimentin was experimentally confirmed by co-immunoprecipitation experiments: the Par-4 antibody co-immunoprecipitated endogenous vimentin, and the vimentin antibody co-immunoprecipitated endogenous Par-4. Immunocytochemical analysis confirmed that Par-4 co-localized with vimentin. On the other hand, cells treated with Arylquin 1 showed neither Par-4 co-immunoprecipitation nor co-localization with vimentin, indicating that Arylquin 1 displaced Par-4 from vimentin. This action of Arylquin 1 was not associated with inhibition of vimentin expression, suggesting that Arylquin 1 may cause conformational changes in vimentin to inhibit its ability to bind and sequester Par-4 or compete for a hydrophobic binding region on vimentin crucial for Par-4 binding. The differential regulation of Par-4 secretion in normal and various cancer cells by Arylquin 1 may reflect distinct posttranslational modification patterns of Par-4 and/or vimentin; studies are underway to address the underlying mechanism.

Computer modeling using molecular dynamics simulations led to a minimum-energy structure in which Arylquin 1 binds tetrameric vimentin in a hydrophobic pocket that lies between a pair of head-to-tail α-helical dimers. The spatial arrangement of functional groups within Arylquin 1 was ideally suited to stabilize binding to vimentin. Additional modeling revealed that Arylquin 1 and its analogs examined bind vimentin in the same orientation but with different binding energies. The relative values of the calculated binding energies are qualitatively consistent with experimental trends: Arylquin 1, Arylquin 6 and Arylquin 8 with the largest binding energies promoted the highest levels of Par-4 secretion. The fluorine group in Arylquin 1 was indispensable for activity, and the removal of the fluorine was accompanied by reduced binding and concomitant loss of Par-4 secretory.

Figure 2:
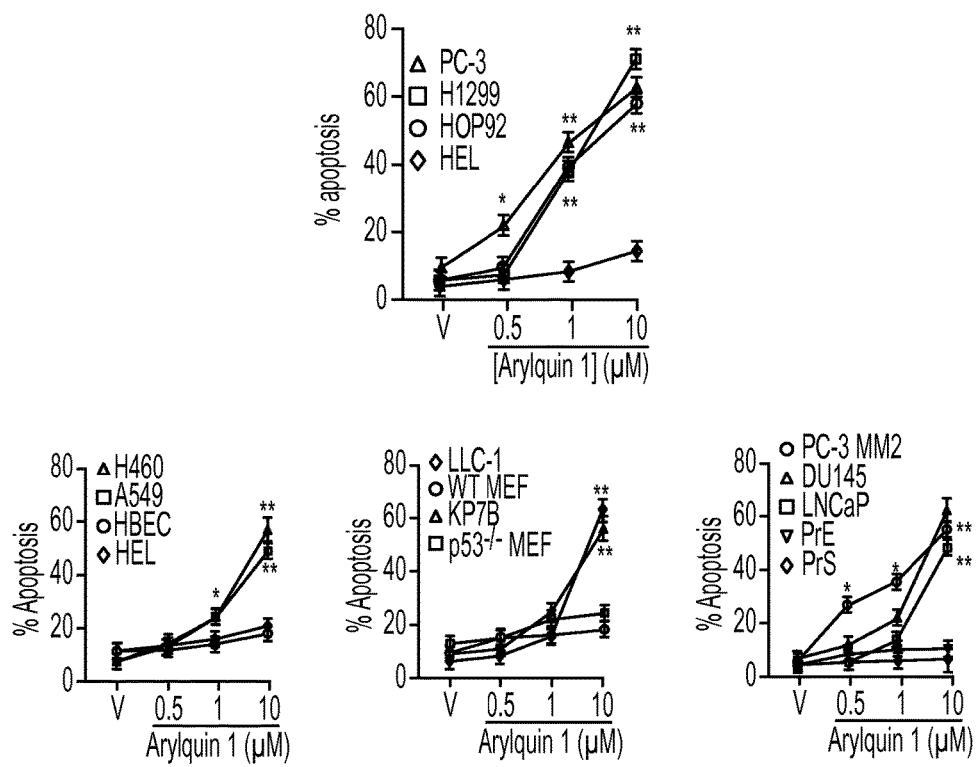
FIG. 2 shows charts illustrating the induced apoptosis in cancer cells by an arylquinoline of the present disclosure. Normal cells (MEFs, HELs, HBEC, PrE, prostate stromal cells PrS) or lung cancer cells (human A549 and H460, mouse LLC1 and KP7B) and prostate cancer cells (PC-3 MM2, DU145, LNCaP) were treated with the indicated amounts (0.5, 1 and 10 µM) of Arylquin 1 or vehicle (V) for 24 h, and apoptosis was determined by ICC for active caspase-3. Data shown represent mean values from three independent experiments±s.d. Asterisks (**) or (*) indicate statistical significance (P<0.0001) or (P<0.001), respectively, by the Student t test.

Because targeting vimentin may induce apoptosis, we tested normal cells and diverse cancer cells for apoptosis by Arylquin 1. Arylquin 1 induced the dose-dependent apoptosis in cancer cells but not in normal cells (FIG. 2). Importantly, 500 nM amounts of Arylquin 1, which triggered secretion of Par-4 from normal cells but not lung cancer cells, did not directly induce apoptosis in normal or cancer cells. By contrast, 500 nM amounts of Arylquin 1 induced apoptosis of PC-3 cells and its derivative PC-3MM2, which are sensitive to apoptosis by Par-4, but not in LNCaP or DU145 cells, which are resistant to apoptosis by Par-4.

Figure 3:
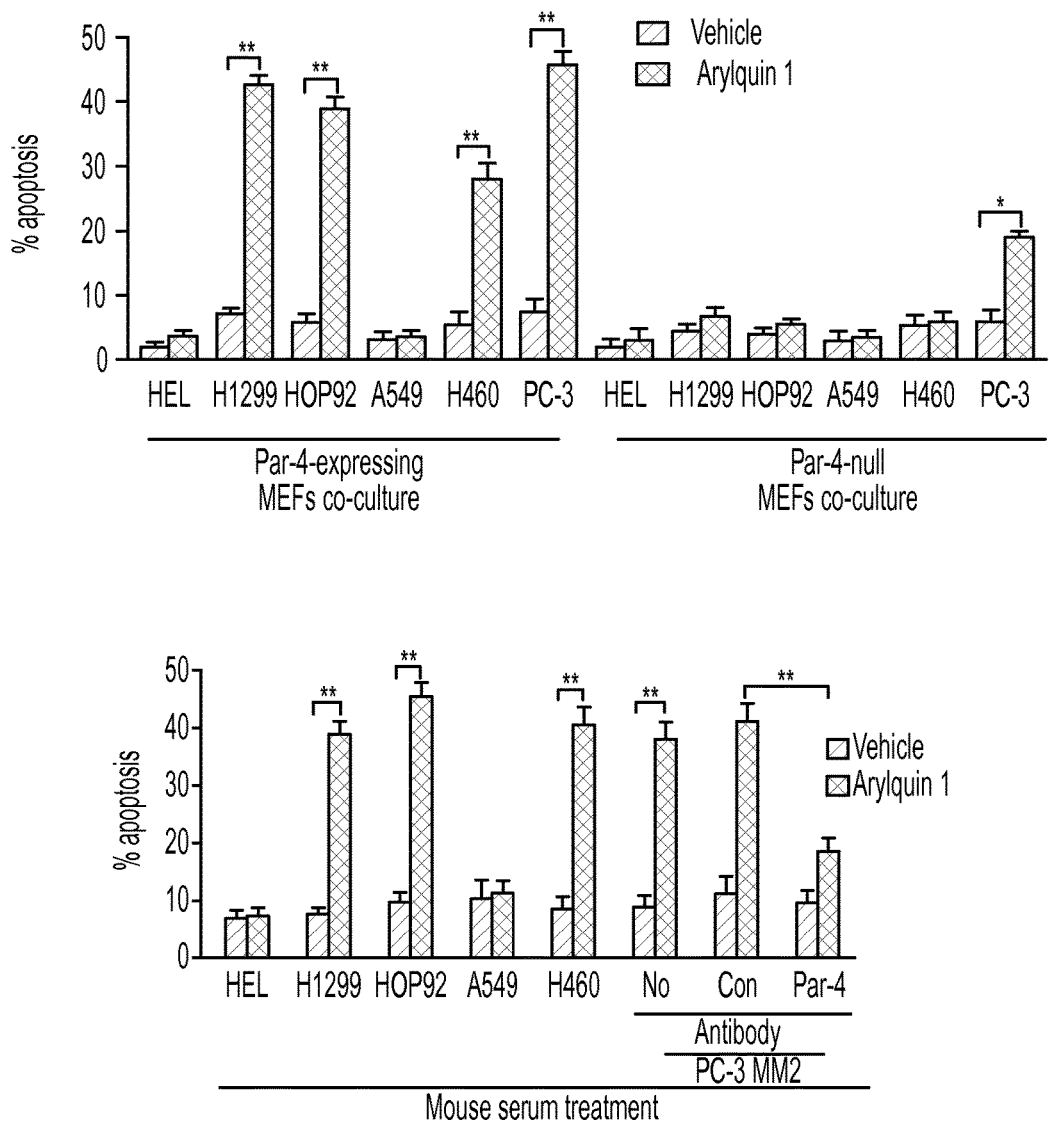
FIG. 3 shows apoptosis activity for an arylquinoline of the present disclosure. Top: Cancer cells were co-cultured with MEFs and treated with Arylquin 1 (500 nM) or vehicle and tested for apoptosis. Bottom: Serum from mice injected with Arylquin 1 (Aq) or corn oil vehicle (V), was examined by Western blot analysis (not shown). Aliquots of serum from these mice were either directly added to the growth medium of cells in culture, or incubated with the indicated antibody, and then added to the growth medium of PC-3 MM2 cells to test for apoptosis.
Figure 4:
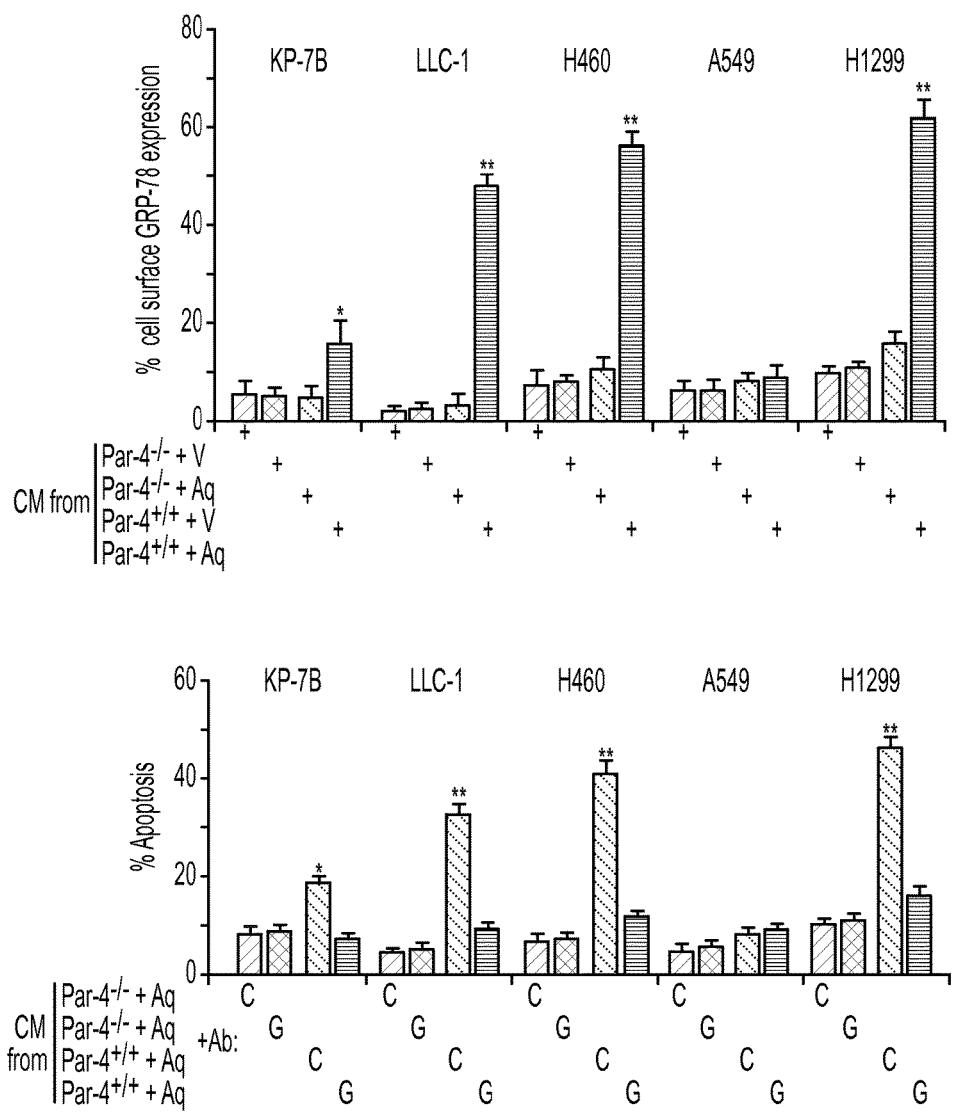
FIGS. 4A and 4B are bar graphs illustrating percent cell surface GRP-78 expression and apoposis activity for an arylquinoline of the present disclosure.
Figure 5:
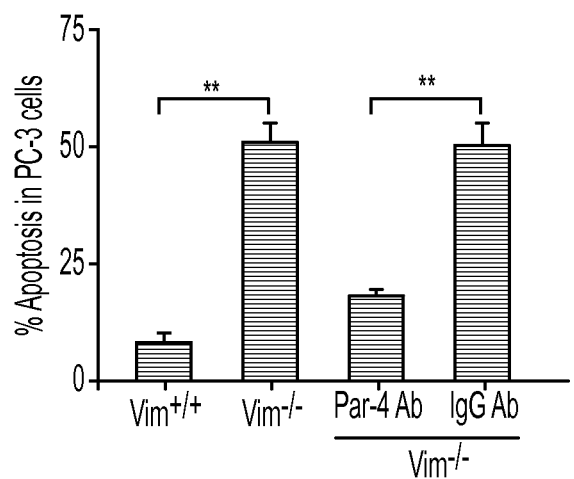
FIG. 5 is a bar graph showing apoptosis activity in PC-3 cells. The CM from Vim−/− MEFs was treated with the indicated antibody (Ab) and tested for apoptosis of cancer cells. The CM from Vim+/+ or Vim−/− cells served as additional controls. Data shown represent mean values from three independent experiments±s.d. Asterisks (**) indicate statistical significance (P<0.0001) by the Student t test.

We next tested co-cultures of normal cells with cancer cells for the apoptotic effect of Arylquin 1 at 500 nM, as this low concentration induced the secretion of Par-4 from normal cells yet did not induce apoptosis in normal or cancer cells. Arylquin 1 treatment of the co-cultures containing Par-4$^{+/+}$ MEFs and cancer cells resulted in apoptosis of the cancer cells, relative to vehicle-treatment (FIG. 3 top). Only the cancer cells, but not normal HEL cells, underwent apoptosis in such co-culture experiments. By contrast, Arylquin 1 treatment of the co-cultures containing Par-4$^{-/-}$ MEFs and cancer cells did not induce apoptosis. Paracrine apoptosis induced in the cancer cells by Par-4, which was secreted from Par-4$^{+/+}$ MEFs but not Par-4$^{-/-}$ MEFs in response to Arylquin 1 treatment, was mediated via cell surface GRP78 (FIG. 4). Moreover, vimentin-deficient cells showed robust increase in secretion of pro-apoptotic Par-4 activity in the CM relative to counterpart wild type cells, and Arylquin 1 did not further induce Par-4 secretion in these cells (FIG. 5). Based on these findings, we infer that: (a) vimentin sequestered Par-4 and prevented its secretion, and (b) Arylquin 1 bound to vimentin and thereby altered the vimentin-Par-4 association to facilitate Par-4 secretion.

To determine the physiological significance of these findings, we injected immunocompetent mice with Arylquin 1 or vehicle and examined their serum for circulating levels of Par-4. Arylquin 1 produced 5-fold higher Par-4 secretion relative to vehicle control in serum (FIG. 3 bottom). Serum from the Arylquin 1 treated mice, but not vehicle-treated mice, produced significantly higher (P<0.001) ex vivo apoptosis of cancer cell cultures (FIG. 3 bottom). The pro-apoptotic activity in the serum was neutralized by the Par-4 antibody. These findings implied that systemic Par-4 levels were elevated in response to Arylquin 1 treatment and that these levels were effective in producing apoptosis of cancer cells.

In summary, the present study identified a novel secretagogue, Arylquin 1, that produced a dose-dependent secretion of Par-4 at nanomolar concentrations from both normal fibroblasts and epithelial cells. Vimentin was the primary target of Arylquin 1, as determined using a biotinylated analog of Arylquin 1. Vimentin represents a particularly important therapeutic target because of its elevation in diverse tumors and its causal role in EMT and metastasis [12]. Importantly, this chemical genetics approach led to the identification of vimentin as a novel binding partner of Par-4 and indicated that Arylquin 1 exhibited its function by binding to vimentin and releasing vimentin-bound Par-4 for secretion. At low concentrations, Arylquin 1 by itself did not kill normal cells and most cancer cells, but instead, it caused robust secretion of Par-4 from normal cells and triggered apoptosis in cancer cells only when they were used in co-culture experiments with normal cells. These findings, which implicated Par-4 secreted from normal cells in the apoptotic death of cancer cells, were corroborated by the observation that Arylquin 1 treatment of cancer cells co-cultured with Par-4-null normal cells failed to induce apoptosis of the cancer cells. Thus, Arylquin 1 induced paracrine apoptosis in cancer cells via Par-4 secreted by normal cells. Because Par-4 produced apoptosis in diverse tumors and because there were no previously reported compounds that acted at nanomolar concentrations to produce the levels of Par-4 secretion discovered in this study, these findings have potential, translational significance.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method for alleviating, ameliorating, or lessening the severity of cancer in a subject in need thereof comprising administering to the subject an effective amount of the compound of formula (I):

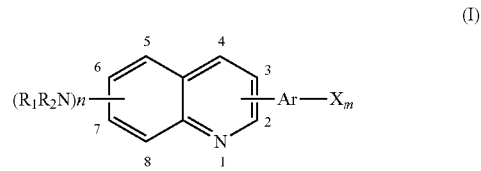

or a pharmaceutically acceptable salt thereof;
wherein n is 1, 2, 3, 4, 5, or 6, for each $NR_1R_2$, $R_1$ and $R_2$ are independently H, alkyl, alkoxy, aryl, heteroaryl; Ar is aryl or heteroaryl, which can be further substituted with halogen, amino, alkylamino, dialkylamino, arylalkylamino, N-oxides of dialkylamino, trialkylammonium, mercapto, alkylthio, alkanoyl, nitro, nitrosyl, cyano, alkoxy, alkenyloxy, aryl, heteroaryl, sulfonyl, sulfonamide, $CONR_3R_4$, $NR_3CO(R_4)$, $NR_3COO(R_4)$, $NR_3CONR_4R_5$ where $R_3$, $R_4$, $R_5$, are independently, H, alkyl, aryl, heteroaryl or a fluorine; X represents halogen; m is 1, 2, 3, 4, or 5,
wherein the cancer is selected from prostate cancer or lung cancer.

2. The method according to claim 1, wherein n is 2 and one $NR_1R_2$ group is at the 2 position of the quinoline ring and the another $NR_1R_2$ group is at the 7 position of the quinoline ring and the Ar-Xm group is at the 3 position of the quinoline ring.

3. The method according to claim 2, wherein m is 1 or 2, Ar is phenyl and X is selected from fluoro or chloro.

4. The method according to claim 2, wherein Ar is heteroaryl.

5. A compound according to formula (I):

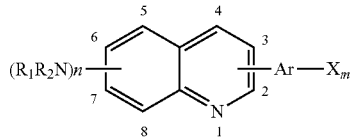

or a pharmaceutically acceptable salt thereof;
wherein n is 1, 2, 3, 4, 5, or 6, for each $NR_1R_2$, $R_1$ and $R_2$ are independently H, alkyl, alkoxy, aryl, heteroaryl; Ar is aryl or heteroaryl, which can be further substituted with halogen, amino, alkylamino, dialkylamino, arylalkylamino, N-oxides of dialkylamino, trialkylammonium, mercapto, alkylthio, alkanoyl, nitro, nitrosyl, cyano, alkoxy, alkenyloxy, aryl, heteroaryl, sulfonyl, sulfonamide, $CONR_3R_4$, $NR_3CO(R_4)$, $NR_3COO(R_4)$, $NR_3CONR_4R_5$ where $R_3$, $R_4$, $R_5$, are independently, H, alkyl, aryl, heteroaryl or a fluorine; X represents halogen; m is 1, 2, 3, 4, or 5.

6. The compound of claim 5, wherein n is 1 or 2; for each $NR_1R_2$, $R_1$ and $R_2$ are independently H, or a lower alkyl; Ar is phenyl; m is 1 or 2; and X is selected from fluoro or chloro.

7. The compound of claim 5, wherein the compound is 3-(2-fluorophenyl)-$N^7$,$N^7$-dimethylquinoline-2,7-diamine; 3-(3-fluorophenyl)-$N^7$,$N^7$-dimethylquinoline-2,7-diamine; 3-(4-fluorophenyl)-$N^7$,$N^7$-dimethylquinoline-2,7-diamine; 3-(2-fluorophenyl)-N,N-dimethylquinolin-7-amine; 3-(2-fluorophenyl)quinolin-2-amine.

8. A biotinylated derivative of the compound according to claim 5.

9. A pharmaceutically acceptable composition comprising a compound of claim 5 and a pharmaceutically acceptable additive.

10. A method of alleviating, ameliorating, or lessening the severity of cancer in a subject in need thereof comprising administering to the subject an effective amount of a pharmaceutically acceptable composition of claim 9, wherein the cancer is selected from prostate or lung cancer.

11. The method of claim 1, wherein n is 2; $R_1$ and $R_2$ are independently H, or alkyl; Ar is aryl substituted with alkoxy; and m is 1; and wherein one $NR_1R_2$ group is at the 2 position of the quinoline ring and the another $NR_1R_2$ group is at the 7 position of the quinoline ring and the Ar-Xm group is a the 3 position of the quinoline ring and X is selected from the fluoro or chorlo.

12. The compound of claim 5, wherein n is 2; $R_1$ and $R_2$ are independently H, or alkyl; Ar is aryl substituted with alkoxy; and m is 1; and wherein one $NR_1R_2$ group is at the 2 position of the quinoline ring and the another $NR_1R_2$ group is at the 7 position of the quinoline ring and the Ar-Xm group is at the 3 position of the quinoline ring and X is selected from fluoro or chloro.

13. The pharmaceutically acceptable composition of claim 9, wherein n is 2; $R_1$ and $R_2$ are independently H, or alkyl; Ar is aryl substituted with alkoxy; and m is 1 ; and wherein one $NR_1R_2$ group is at the 2 position of the quinoline ring and the another $NR_1R_2$ group is at the 7 position of quinoline ring and the Ar-Xm group is at the 3 position of quinoline ring and X is selected from fluoro or chloro.

* * * * *